(12) United States Patent
Adachi et al.

(10) Patent No.: US 11,638,809 B2
(45) Date of Patent: May 2, 2023

(54) TRIPTAN MICROPORATION DELIVERY SYSTEM

(71) Applicant: PASSPORT TECHNOLOGIES, INC., San Diego, CA (US)

(72) Inventors: Hirotoshi Adachi, San Diego, CA (US); Shohei Horie, San Diego, CA (US); Akinori Hanatani, San Diego, CA (US); Masato Nishimura, Osaka (JP); Yuki Yamada, San Diego, CA (US); Joe Hua, Rosemead, CA (US)

(73) Assignee: Passport Technologies, Inc., San Diego, CA (US)

( * ) Notice: Subject to any disclaimer, the term of this patent is extended or adjusted under 35 U.S.C. 154(b) by 308 days.

(21) Appl. No.: 16/911,181

(22) Filed: Jun. 24, 2020

(65) Prior Publication Data

US 2020/0406015 A1 Dec. 31, 2020

Related U.S. Application Data

(60) Provisional application No. 62/868,697, filed on Jun. 28, 2019.

(51) Int. Cl.
| | |
|---|---|
| *A61M 37/00* | (2006.01) |
| *A61K 9/70* | (2006.01) |
| *A61K 31/4196* | (2006.01) |
| *A61K 31/4045* | (2006.01) |
| *A61K 47/40* | (2006.01) |
| *A61K 47/26* | (2006.01) |
| *A61K 47/12* | (2006.01) |
| *A61K 31/422* | (2006.01) |
| *A61N 1/32* | (2006.01) |

(52) U.S. Cl.
CPC .......... *A61M 37/00* (2013.01); *A61K 9/7084* (2013.01); *A61K 31/4045* (2013.01); *A61K 31/4196* (2013.01); *A61K 31/422* (2013.01); *A61K 47/12* (2013.01); *A61K 47/26* (2013.01); *A61K 47/40* (2013.01); *A61M 2037/0007* (2013.01); *A61N 1/327* (2013.01)

(58) Field of Classification Search
CPC .................................................. A61M 37/00
See application file for complete search history.

(56) References Cited

U.S. PATENT DOCUMENTS

| | | | |
|---|---|---|---|
| 6,922,578 B2 | 7/2005 | Eppstein et al. | |
| 7,141,034 B2 | 11/2006 | Eppstein et al. | |
| 7,384,396 B2 | 6/2008 | Samuels et al. | |
| 7,392,080 B2 | 6/2008 | Eppstein et al. | |
| 7,758,561 B2 | 7/2010 | Eppstein | |
| 7,914,813 B2 | 3/2011 | Adachi et al. | |
| 8,517,958 B2 | 8/2013 | Eppstein et al. | |
| 8,641,689 B2 | 2/2014 | Messier et al. | |
| 8,706,210 B2 | 4/2014 | Eppstein et al. | |
| 9,144,671 B2 | 9/2015 | Cantor et al. | |
| 9,272,137 B2 | 3/2016 | Anderson et al. | |
| 9,486,616 B2 | 11/2016 | Eppstein et al. | |
| 9,498,609 B2 | 11/2016 | Tagliaferri et al. | |
| 9,579,380 B2 | 2/2017 | Eppstein | |
| 9,918,665 B2 | 3/2018 | McRae et al. | |
| 10,010,453 B2 | 7/2018 | Harima et al. | |
| 10,166,378 B2 | 1/2019 | Tagliaferri et al. | |
| 2007/0250018 A1 | 10/2007 | Adachi et al. | |
| 2010/0209484 A1* | 8/2010 | Choi | A61K 9/7038 424/449 |
| 2019/0070103 A1 | 3/2019 | Ameri et al. | |
| 2020/0023173 A1 | 1/2020 | Smith et al. | |

FOREIGN PATENT DOCUMENTS

| | | |
|---|---|---|
| AU | 2014202524 A1 | 5/2014 |
| AU | 2016231468 A1 | 10/2016 |
| EP | 3 311 762 B1 | 7/2020 |
| EP | 3 411 110 B1 | 8/2020 |
| WO | WO 2012/075209 A1 | 6/2012 |
| WO | WO 2017/143345 A1 | 8/2017 |

OTHER PUBLICATIONS

Hanumanaik, Met a/(2012) "Design, Evaluation and Recent Trends in Transdermal Dr" *International Journal of Pharmaceutical Sciences and Research* 3(08): 2393-2406.
Subedi, RK etal (2011) "Influence of formulation variables in transdermal drug deliver" *International Journal of Pharmaceutics* 419: 209-214.
International Preliminary Report on Patentability (Chapter I) issued in application No. PCT/US2020/039427, dated Jan. 6, 2022.

* cited by examiner

*Primary Examiner* — Rei Tsang Shiao
(74) *Attorney, Agent, or Firm* — Knobbe, Martens, Olson & Bear, LLP

(57) ABSTRACT

A transdermal delivery system for delivery of a triptan into a tissue membrane of a subject. The system includes a transdermal microporation apparatus for heating a skin surface and a triptan drug delivery patch. The drug delivery patch comprises a top layer comprising an adhesive, a middle layer comprising the triptan, and a bottom layer. A method for treating a subject comprises identifying a subject having a migraine, using the transdermal microporation apparatus to open a plurality of micropores in the skin of the subject, and applying the triptan drug delivery patch to the subject's skin over the micropores for a period of time effective to deliver the triptan through the micropores in an amount effective to treat the subject's migraine.

20 Claims, 18 Drawing Sheets

TRIPTAN MICROPORATION DELIVERY SYSTEM

CROSS REFERENCE TO RELATED APPLICATIONS

This application claims the benefit of U.S. provisional application No. 62/868,697 filed on Jun. 28, 2019, which is hereby incorporated herein by reference in its entirety.

BACKGROUND

Field

This application relates to compositions, devices and methods for transdermal drug delivery, and in particular to triptan compositions and methods for administering the triptan to subjects by transdermal microporation devices.

Description

Migraine is a condition that affects approximately 10% of the adult population worldwide, yielding approximately 600 million people with about 28 million in the United States alone. Females suffer from migraine headaches three-fold more frequently than males. Migraine headache is associated with inflamed and dilated blood vessels leading to severe unilateral pain that worsens with physical activity. Approximately one-fifth of migraine patients experience an aura or visual symptoms, such as spots of light, zigzag lines, or a graying out of vision. Migraines typically last for up to 24 hours but can range from 4 to 72 hours and patients often experience migraine attacks one two times per month.

Migraines can be triggered by many different factors, including life stressors, certain foods or dietary habits, shifts in circadian rhythms, schedules or sleep patterns and changes in weather such as barometric pressure or altitudes as well as cyclic variation in hormonal levels during the menstrual cycle. Pharmacologic interventions constitute the mainstay of treatment for migraines and are available for both acute treatment (abortive) and prevention (prophylactic).

Triptans are serotonin receptor agonists that can be used to treat acute migraines of moderate to severe intensity. When these agents are used early in the course of an attack, triptans abort more than 80% of migraines within two hours. However, several different triptan products are available with variations in the efficacy and tolerability of different medications in this class. Triptans are also available in a variety of formulations. Non-oral formulations are typically used for patients with gastrointestinal symptoms of nausea or vomiting and when a more rapid onset of action is desired. Triptans are thought to work by activating serotonin (5-HT) receptors on trigeminovascular nerve endings, inhibiting the release of neurotransmitters that cause painful cranial vasodilation. Furthermore, triptans produce active vasoconstriction and may relieve symptoms of migraine by stimulating 5-HT receptors on cranial vessels. Oral tablets containing triptans generally have insufficient efficacy and lack sufficiently fast onset. Subcutaneous injections show higher efficacy and fast onset, but they sometimes induce severe adverse effects. Oral and nasal routes often cause undesirable taste problems and are difficult administrations for nausea and vomiting migraine patients.

Passive transdermal drug delivery is a convenient and effective way to administer a variety of therapeutics. This route of administration is both noninvasive and produces steady drug delivery over an extended period of time. While conventional transdermal systems (such as drug patches) have demonstrated the benefits of delivering drugs via the skin, they only work for an extremely limited number of drugs. This is because millions of dead skin cells form a protective barrier on the surface of the skin (the stratum corneum) that prevents most therapeutic molecules from passing into the skin.

The stratum corneum is chiefly responsible for the barrier properties of skin. Thus, it is this layer that presents the greatest barrier to transdermal flux of drugs or other molecules into the body and of analytes out of the body. The stratum corneum, the outer horny layer of the skin, is a complex structure of compact keratinized cell remnants separated by lipid domains. Compared to the oral or gastric mucosa, the stratum corneum is much less permeable to molecules either external or internal to the body. The stratum corneum is formed from keratinocytes, which comprise the majority of epidermal cells that lose their nuclei and become corneocytes. These dead cells comprise the stratum corneum, which has a thickness of only about 10-30 microns and protects the body from invasion by exogenous substances and the outward migration of endogenous fluids and dissolved molecules. The stratum corneum is continuously renewed by shedding of corneum cells during desquamination and the formation of new corneum cells by the keratinization process.

Historically, the majority of drugs have been delivered orally or by injection. However, neither the oral or injection route is well-suited for continual delivery of drugs over an extended period of time. Further, the injection method of administration is inconvenient and uncomfortable; additionally, needles continue to pose a hazard after their use. Therefore, transdermal drug delivery to the body has been a popular and efficacious method for delivering a limited number of permeants into an organism.

Passive transdermal patches are typically limited to lipid-soluble drugs with a molecular weight of fewer than 500 daltons. To enhance transdermal drug delivery, there are known methods for increasing the permeability of the skin to drugs. For example, U.S. Pat. No. 8,116,860 describes transdermal permeant delivery systems and methods that painlessly create aqueous micropores in the stratum corneum within a few milliseconds. These aqueous channels enable water-soluble drugs to flow from a transdermal patch, enter the viable epidermis and then the systemic circulation. The patch may be formulated to provide for bolus or sustained transdermal delivery.

Transdermal permeant delivery systems are being developed under the PASSPORT tradename. The PASSPORT system comprises a reusable handheld applicator and a single-use porator with drug patch. Pressing the activation button of the applicator releases a pulse of energy to the porator. The rapid conduction of this energy into the surface of the skin painlessly ablates the stratum corneum under each filament to create the microchannels. A simple transdermal patch is then applied to the ablated skin and drug delivery begins.

An iontophoretic system for the transdermal delivery of a triptan was approved by the U.S. Food and Drug Administration (FDA) in 2013. This system, sold under the tradename ZECUITY, used a battery-powered iontophoretic patch to deliver sumatriptan. However, in 2016 it was withdrawn from the market after the manufacturer received postmarketing reports of application site reactions described as "burn" and/or "scar" in patients treated with ZECUITY. Descriptions of these reactions included severe redness, cracked skin, blistering or welts, and burns or scars where the patch was worn. Patients described severe pain, itching, or burning. Although many cases resolved within hours to weeks, there were reports of cases with unresolved skin reactions, typically skin discoloration, after several months.

Thus, there remains a long-felt need for improved compositions, devices and methods for the transdermal delivery of triptans.

SUMMARY OF THE INVENTION

In some aspects, a patch for delivering a triptan drug to a subject in need thereof is described herein. The patch may comprise a top layer comprising an adhesive, a middle layer comprising a triptan, and a bottom layer, wherein the bottom layer comprises a release liner.

In some embodiments, the middle layer further comprises a skin irritation reducer.

In some embodiments, the middle layer further comprises a stabilizer in an amount in the range of about 0.01 g/cm$^2$ to about 0.5 g/cm$^2$.

In some embodiments, the molar ratio of the amounts of the triptan and skin irritation reducer are in a range of from about 1:0.5 to about 1:2.

In some embodiments, the triptan is selected from sumatriptan, rizatriptan, or zolmitriptan.

In some embodiments, the skin irritation reducer is an organic acid or salt thereof.

In some embodiments, the organic acid is selected from ascorbic acid, citric acid, succinic acid, tartaric acid, maleic acid, lactic acid, benzoic acid, and sorbic acid or a combination thereof.

In some embodiments, the stabilizer is a saccharide.

In some embodiments, the saccharide is selected from mannitol, maltose, trehalose, xylitol, xylose, dextrose, lactose, sorbitol, sucrose, fructose, maltitol, erythritol, lactitol, isomalt, and cyclodextrins or a combination thereof.

In some embodiments, the middle layer further comprises a reservoir that is configured to contain the triptan.

In some embodiments, the reservoir comprises a matrix.

In some embodiments, the matrix has a water holding capacity in the range of about 0.1 mg/cm$^2$ to about 10 mg/cm$^2$.

In some embodiments, the matrix comprises a non-woven fabric.

In some embodiments, the matrix has a thickness in the range of about 10 μm to about 100 μm.

In some embodiments, the matrix areal weight is in the range of about 10 g/m$^2$ to about 100 g/m$^2$.

In some embodiments, the size of the matrix is in the range of about 0.25 cm$^2$ to about 5 cm$^2$.

In some embodiments, the patch further comprising an anti-microbial agent.

In some embodiments, the anti-microbial agent is selected from at least one of benzoic acid, methyl paraben, propyl paraben, benzalkonium chloride, chlorhexidine, cresol, salicylic acid, sorbic acid, and benzetonium chloride, or combination thereof.

In some embodiments, the skin irritation reducer a non-organic acid or salt thereof.

In some embodiments, the non-organic acid is selected from hydrochloric acid, phosphoric acid, boric acid, and acetic acid.

In some embodiments, the matrix comprises about 0.1 to about 5.0 mg/cm$^2$ zolmitriptan.

In some embodiments, the amounts of the zolmitriptan and the skin irritation reducer are in a range from about 1:0.75 to about 1:1.15.

In some embodiments, the size of the matrix is in the range of about 0.25 cm$^2$ to about 4 cm$^2$.

In some embodiments, the stabilizer is sucrose.

In some embodiments, the total amount per unit area of the matrix with zolmitriptan and the stabilizer is 0.05 to 0.5 mg/cm$^2$.

In some aspects, a method of treating a subject in need thereof is described herein. The method may comprise identifying a subject having a migraine, opening a plurality of micropores in the skin of the subject, applying a patch to the subject's skin over the micropore for a period of time, wherein the patch comprises: a top layer comprising an adhesive, a middle layer comprising a triptan, and a bottom layer, wherein the bottom layer comprises a release liner, wherein the period of time is selected to deliver a therapeutically effective amount of the triptan through the plurality of micropores.

In some embodiments, the middle layer further comprises a skin irritation reducer and a stabilizer.

In some embodiments, the opening of the plurality of micropores in the skin of the subject comprises applying a transdermal microporation apparatus to the subject's skin.

In some embodiments, the transdermal microporation is a thermal tissue ablation.

In some embodiments, the transdermal microporation creates the micropores through the stratum corneum to the epidermis.

In some embodiments, the transdermal microporation apparatus has a poration energy is about 2 to about 5 mJ/filament.

In some embodiments, the transdermal microporation apparatus has a poration energy density is about 200 to about 500 filaments/cm$^2$.

In some embodiments, the transdermal microporation apparatus has a poration energy density is about 400 filaments/cm$^2$.

In some embodiments, the transdermal microporation poration energy is about 4 mJ/filament and poration energy density is about 400 filaments/cm$^2$.

In some embodiments, the transdermal microporation filament array size is about 0.5 to about 5 cm$^2$.

In some embodiments, the triptan and the skin irritation reducer are in a range from about 1:0.5 to about 1:2.

In some aspects, a transdermal drug delivery patch system for delivering a drug is described herein. The transdermal drug delivery patch system comprises a transdermal microporation apparatus for heating a skin surface; and a triptan drug delivery patch.

In some embodiments, the triptan drug delivery patch system comprises a top layer comprising an adhesive; a middle layer that has at least one reservoir configured to contain the triptan; and a bottom layer, wherein the bottom layer comprises a release liner.

In some embodiments, the middle layer further comprises a skin irritation reducer and a stabilizer.

In some embodiments, the microporation apparatus comprises a conductive member configured to generate heat energy based on a current flowing through the conductive member, and supplying the heat energy to the skin surface in contact with the conductive member during operation.

In some embodiments, the transdermal drug delivery patch system further comprises a power supply configured to provide a current to a conductive member in a plurality of pulses at a supply current value.

These and other embodiments are described in greater detail below.

BRIEF DESCRIPTION OF THE DRAWINGS

The accompanying drawings, which are incorporated in and constitute a part of this specification, illustrate several aspects described below and together with the description, serve to explain the principles of the invention. Like numbers represent the same elements throughout the figures.

DETAILED DESCRIPTION

Figure 1:
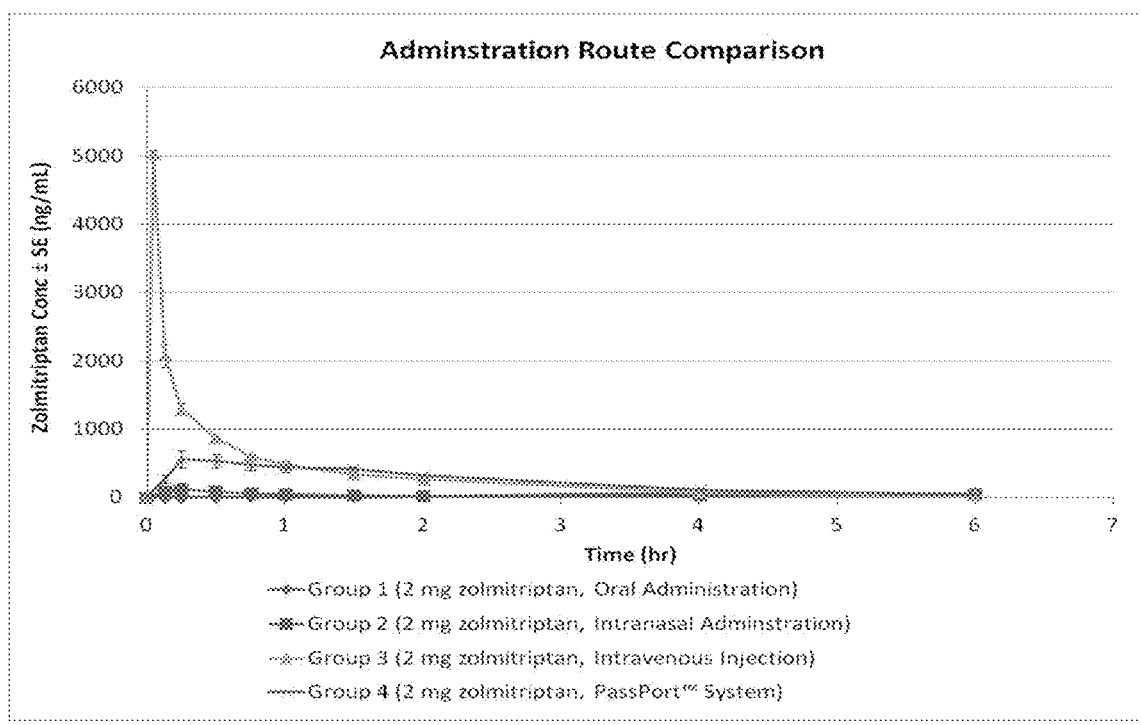
FIG. 1 illustrates the results of an administration route comparison study in hairless rats.

The present invention can be understood more readily by reference to the following detailed description, examples, drawing, and claims, and their previous and following descriptions. However, before the present devices, systems, and/or methods are disclosed and described, it is to be understood that this invention is not limited to the specific devices, systems, and/or methods disclosed unless otherwise specified. It is also to be understood that the terminology used herein is for the purpose of describing particular aspects only and is not necessarily intended to be limiting.

This description is provided as an enabling teaching of the invention. To this end, those skilled in the relevant art will recognize and appreciate that many changes can be made to the various aspects of the invention described herein, while still obtaining beneficial results. It will also be apparent that some of the desired benefits can be obtained by selecting some of the features described herein without utilizing other features. Accordingly, those who work in the art will recognize that many modifications and adaptations to the present description are possible and can even be desirable in certain circumstances and are a part of the present invention. Thus, this description is provided as illustrative of certain principles of the present invention and not in limitation thereof.

Definitions

As used throughout, the singular forms "a," "an," and "the" include plural referents unless the context clearly dictates otherwise. Thus, for example, reference to "a filament" can include two or more such filaments unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, "stratum corneum" refers to the outermost layer of the skin, consisting of from about 15 to about 20 layers of cells in various stages of drying out. The stratum corneum provides a barrier to the loss of water from inside the body to the external environment and from attack from the external environment to the interior of the body.

As used herein, "tissue" refers to an aggregate of cells of a particular kind, together with their intercellular substance, that forms a structural material. At least one surface of the tissue must be accessible to the device. The preferred tissue is the skin. Other tissues suitable for use with this invention include mucosal tissue and soft organs.

As used herein, the term, "interstitial fluid" is the clear fluid that occupies the space between the cells in the body. As used herein, the term "biological fluid" is defined as a fluid originating from a biological organism, including blood serum or whole blood as well as interstitial fluid.

As used herein, a "tissue membrane" can be any one or more epidermal layers of a subject. For example, in one aspect, the tissue membrane is a skin layer that includes the outermost layer of the skin, i.e., the stratum corneum. In an alternative aspect, a skin layer can include one or more backing layers of the epidermis, commonly identified as stratum granulosum, stratum malpighii, and stratum germinativum layers. It will be appreciated by one of ordinary skill in the art that there is essentially little or no resistance to transport or to absorption of a permeant through the backing layers of the epidermis. Therefore, in one aspect, an at least one formed pathway in a skin layer of a subject is a pathway in the stratum corneum layer of a subject. Further, as used herein, "stratum corneum" refers to the outermost layer of the skin, typically containing from about 15 to about 20 layers of cells in various stages of drying out. The stratum corneum provides a barrier to the loss of water from inside the body to the external environment and from attack from the external environment to the interior of the body. Still further, as used herein, "tissue membrane" can refer to an aggregate of cells of a particular kind, together with their intercellular substance, that forms a structural material. In various embodiments at least one surface of the tissue membrane is accessible to one or more of the poration devices and/or permeant compositions described herein. As noted above, the preferred tissue membrane is the skin. Other tissues suitable for use with such devices and compositions include mucosal tissue and soft organs.

As used herein, the term, "subcutaneous fluid" can include, without limitation, moisture, plasma, blood, one or more proteins, interstitial fluid, and any combination thereof. In one aspect, a subcutaneous fluid according to this description is a moisture source comprising water.

As used herein, "poration," "microporation," or any such similar term means the formation of a small hole or crevice (subsequently also referred to as a "micropore") in or through the tissue or biological membrane, such as skin or mucous membrane, or the outer layer of an organism to lessen the barrier properties of this biological membrane for the passage of at least one permeant from one side of the biological membrane to the other for select purposes. Preferably the hole or "micropore" so formed is approximately 1-1000 microns in diameter and extends into the biological membrane sufficiently to break the barrier properties of the stratum corneum without adversely affecting the underlying tissues. It is to be understood that the term "micropore" is used in the singular form for simplicity, but that the microporation devices described herein may form multiple artificial openings. Poration could reduce the barrier properties of a biological membrane into the body for selected purposes, or for certain medical or surgical procedures. For the purposes of this application, "poration" and "microporation" are used interchangeably and mean the same thing.

A "microporator" or "porator" is a component for a microporation device capable of microporation. Examples of a microporator or porator include, but are not limited to, a filament capable of conductively delivering thermal energy via direct contact to a biological membrane to cause the ablation of some portion of the membrane deep enough to form a micropore, an optically heated topical dye/absorber layer, an electromechanical actuator, a microlancet, an array of microneedles or lancets, a sonic energy ablator, a laser ablation system, a high-pressure fluid jet puncturer, and the like. As used herein, "microporator" and "porator" are used interchangeably.

As used herein "penetration" means the controlled removal of cells caused by the thermal and kinetic energy released when the pyrotechnic element explodes which causes cells of the biological membrane and possibly some adjacent cells to be "blown away" from the site. As used herein, "fusible" and "fuse" refer to an element that could remove itself from and electrical circuit when a sufficient amount of energy or heat has been applied to it. i.e., when a resistive, electrically activated poration element is designed to be a fusible element this means that upon activation, during or after the formation of the micropore in the biological membrane, the element breaks, stopping the current flow through it.

As used herein, "penetration enhancement" or "permeation enhancement" means an increase in the permeability of the biological membrane to a drug, bio-active composition, or other chemical molecule, compound, particle or substance (also called "permeant"), so as to increase the rate at which the drug, bio-active composition, or other chemical molecule, compound or particle permeates the biological membrane.

As used herein, "enhancer," "chemical enhancer," "penetration enhancer," "permeation enhancer," and the like includes all enhancers that increase the flux of a permeant, analyte, or other molecule across the biological membrane, and is limited only by functionality. In other words, all cell envelope disordering compounds and solvents and any other chemical enhancement agents are intended to be included. Additionally, all active force enhancer technologies such as the application of sonic energy, mechanical suction, pressure, or local deformation of the tissues, iontophoresis or electroporation are included. One or more enhancer technologies may be combined sequentially or simultaneously. For example, a chemical enhancer may first be applied to permealize the capillary wall and then an iontophoretic or sonic energy field may be applied to actively drive a permeant into those tissues surrounding and comprising the capillary bed.

As used herein, "transdermal" or "percutaneous" means passage of a permeant into and through the biological membrane to achieve effective therapeutic blood levels or local tissue levels of a permeant, or the passage of a molecule or fluid present in the body ("analyte") out through the biological membrane so that the analyte molecule maybe collected on the outside of the body.

As used herein, the term "permeant," "drug," "permeant composition," or "pharmacologically active agent" or any other similar term are used interchangeably to refer to any chemical or biological material or compound suitable for transdermal administration by the methods previously known in the art and/or by the methods taught in the present description, that induces a desired biological or pharmacological effect, which may include but is not limited to (1) having a prophylactic effect on the organism and preventing an undesired biological effect such as an infection, (2) alleviating a condition caused by a disease, for example, alleviating pain or inflammation, and/or (3) either alleviating, reducing, or completely eliminating the disease from the organism. The effect may be local, such as providing for a local anesthetic effect, or it may be systemic. Such substances include broad classes of compounds normally delivered into the body, including through body surfaces and membranes, including skin. In general, for example and not meant to be limiting, such substances can include any bioactive agents such as drug, chemical, or biological material that induces a desired biological or pharmacological effect. To this end, in one aspect, the permeant can be a small molecule agent. In another aspect, the permeant can be a macromolecular agent. In various embodiments, the permeant is a triptan. Examples of triptans include sumatriptan, zolmitriptan, rizatriptan, naratriptan, eletriptan, donitriptan, almotriptan, frovatriptan, avitriptan, LY-334370, L0703,664 and GR 46611.

In various embodiments, transdermal permeant delivery systems and methods that may be used and/or adapted for use with the compositions and methods described herein are described in one or more of U.S. Pat. Nos. 6,022,316, 6,142,939, 6,173,202, 6,183,434, 6,508,785, 6,527,716, 6,692,456, 6,730,028, 7,141,034, 7,392,080, 7,758,561, 8,016,811, 8,116,860, and/or 9,498,609, all of which are hereby incorporated by reference in their entireties and particularly for the purpose of describing such systems and methods. In various embodiments, the transdermal permeant delivery systems commercially available from Nitto Denko Corporation under the PASSPORT tradename may be used or adapted for use in delivering the permeant compositions described herein.

As used herein, an "effective" amount of a pharmacologically active agent means a sufficient amount of a compound to provide the desired local or systemic effect and performance at a reasonable benefit/risk ratio attending any medical treatment. An "effective" amount of a permeation or chemical enhancer as used herein means an amount selected so as to provide the desired increase in biological membrane permeability, the desired depth of penetration, rate of administration, and amount of drug delivered.

As used herein, "animal" or "organism" refers to humans and other living organisms including plants, to which the present invention maybe applied.

As used herein, "analyte" means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, and the like.

As used herein, "transdermal flux rate" is the rate of passage of any analyte out through the skin of an individual, human or animal, or the rate of passage of any permeant, drug, pharmacologically active agent, dye, or pigment in and through the skin of an organism.

As used herein, "non-invasive" means not requiring the entry of a needle, catheter, or other invasive medical instrument into apart of the body.

As used herein, "minimally invasive" refers to the use of mechanical, hydraulic, or electrical means that invade the stratum corneum to create a small hole or micropore without causing substantial damage to the underlying tissues.

As used herein, "pharmaceutically acceptable carrier" refers to a carrier in which a substance such as a pharmaceutically acceptable drug could be provided for deliver. Pharmaceutically acceptable carriers are described in the art, for example, in "Remington: The Science and Practice of Pharmacy," Mack Publishing Company, Pennsylvania, 1995, the disclosure of which is incorporated herein by reference. Carriers could include, for example, water and other aqueous solutions, saccharides, polysaccharides, buffers, excipients, and biodegradable polymers such as polyesters, polyanhydrides, polyamino acids, liposomes and mixtures thereof.

As used herein, "reservoir" refers to a designated area or chamber within a device which is designed to contain a permeant for delivery through an artificial opening in a biological membrane into an organism or may be designed to receive a biological fluid sample extracted from an organism through an artificial opening in a biological membrane. A reservoir could also contain excipient compounds which enhance the effect of a separately contained bioactive permeant. Additionally, a reservoir could contain or be treated with reactive enzymes or reagents designed to allow the measurement or detection of a selected analyte in an extracted biological fluid. A reservoir may be comprised of an open volume space, a gel, a flat planar space which has been coated or treated with a selected compound for subsequent release or reaction, or a permeable solid structure such as a pellet, tablet or porous polymer.

The devices and methods of the present disclosure can be used to transdermally deliver tripans across the skin. In some aspects, the patch may comprise a top layer comprising an adhesive, a middle layer comprising a triptan, and a bottom layer. In some embodiments, the bottom layer comprises a release liner. In some embodiments, the middle layer further comprises a skin irritation reducer. In some embodiments, the middle layer further comprises a stabilizer. In some embodiments, the patch comprises a tissue interface layer.

Examples of suitable tissue interface layers are described in U.S. Pat. No. 7,392,080, which is hereby incorporated herein by reference in its entirety and particularly for the purpose of describing transdermal drug delivery patch systems. In some aspects, a tissue interface layer may comprise some or all of the following: elements for effecting the poration of the tissue, adhesive for attaching the device to the tissue, reservoirs containing permeants for delivery, reservoirs for holding extracted biological fluids, and reagents for assaying an analyte. The tissue interface layer could also include hydrophilic and hydrophobic surface treatments to act as fluid flow modifiers for controlling the motion of liquid permeants or biological fluids collected. The tissue interface layer may also incorporate antimicrobial agents to prevent sepsis or anticlotting or anticoagulents to control the aggregation of permeants or biological fluids extracted. The tissue interface layer may also be treated with permeation enhancers or buffers used for pH stabilization. The tissue interface layer may contain stimuli-responsive polymer gel sections, saturated with beneficial permeants, which could be triggered to release the beneficial permeants through a thermal, chemical or electrical stimulus. The tissue interface layer may release beneficial permeants on demand when heated, for example by the poration elements or other similar elements on the tissue interface layer. The tissue interface layer may contain piezoelectric elements for delivery of acoustic energy into the tissue or permeants being delivered or biological fluids being extracted.

In some aspects, the tissue interface layer may comprise one or more reservoirs. In the case of multiple reservoirs, these reservoirs could be used to keep different and perhaps incompatible permeants separate. Delivery of permeants from the reservoirs could be simultaneously or sequentially. In some embodiments, a reservoir wall may be porated to breach the reservoir membrane and allow the delivery of the permeant into the tissue. This poration of the reservoir is accomplished with the same type of poration elements as are used to porate the tissue. Prior to the breach of this reservoir, the reservoir could maintain a stable, sealed, and sterile environment for the permeant, allowing the entire disposable portion of the integrated device to be manufactured and packaged efficiently and economically. The breaching of the reservoir may occur before, coincidentally with or after the poration of the tissue as required. Additionally, the flux rate of a permeant from a particular reservoir into the tissue is proportional to the area of the micropore coupling the reservoir to the biological membrane, if all other factors such as micropore density or iontophoretic current are the same. A reservoir could initially be empty or contain an absorbent material, in order to serve as a storage location for extracted biological fluids. Reagents for the assay of an analyte in the biological fluid would typically be located at the entrance to the extracted biological fluid storage reservoir.

Further, as used herein, "triptan", means a class or family of tryptamine-based drugs used as abortive medication in the treatment of migraines and cluster headaches. Examples of triptans include, but is not limited to, sumatriptan, rizatriptan, naratriptan, eletriptan, donitriptan, almotriptan, frovatriptan, avitriptan, and zolmitriptan. In some embodiments, the triptan comprises zolmitriptan, sumatriptan, or rizatriptan. In some embodiments, the triptan comprises zolmitriptan.

In some aspects, the skin irritation reducer is an organic acid. In some embodiments, the skin irritation reducer is a salt form of the organic acid. In some embodiments, the organic acid is selected from ascorbic acid, citric acid, succinic acid, tartaric acid, maleic acid, lactic acid, benzoic acid, and sorbic acid or a combination thereof. In some embodiments, the skin irritation reducer is selected a non-organic acid. In some embodiments, the skin irritation reducer is a salt form of the non-organic acid. In some embodiments, the non-organic acid is hydrochloric acid, phosphoric acid, boric acid, acetic acid or a combination thereof. In some embodiments, the non-organic acid is evaporated during the manufacturing process.

In some aspects, the stabilizer is a saccharide. In some embodiments, the saccharide is selected from mannitol, maltose, trehalose, xylitol, xylose, dextrose, lactose, sorbitol, sucrose, fructose, maltitol, erythritol, lactitol, isomalt, and cyclodextrin or a combination thereof. In some embodiments, the stabilizer is sucrose.

In some embodiments, the molar ratio of the amounts of the triptan and the skin irritation reducer in the patch are in a range from about 1:0.5 to about 1:2. In some embodiments, the triptan and the skin irritation reducer are in a molar ratio in the range from about 1:0.75 to about 1:1.5.

In some aspects, the middle layer of the patch comprises a reservoir. In some embodiments, the reservoir comprises about 0.1% to about 90% by weight triptan. In some embodiments, the triptan comprises approximately 20 weight % to approximately 80 weight % of the middle layer, including amounts such as 25 weight %, 30 weight %, 35 weight %, 40 weight %, 45 weight %, 50 weight %, 55 weight %, 60 weight %, 65 weight %, 70 weight %, and 75 weight % of the middle layer, and including any range of weight percentages derived from these values.

In some embodiments, the middle layer comprises about 0.1% to about 90% by weight of a stabilizer. In some embodiments, the stabilizer comprises approximately 20 weight % to approximately 80 weight % of the middle layer, including amounts such as 25 weight %, 30 weight %, 35 weight %, 40 weight %, 45 weight %, 50 weight %, 55 weight %, 60 weight %, 65 weight %, 70 weight %, and 75 weight % of the middle layer, and including any range of weight percentages derived from these values.

In some embodiments, the middle layer comprises about 0.1 to about 90% by weight of a skin irritation reducer. In some embodiments, the skin irritation reducer comprises approximately 20 weight % to approximately 80 weight % of the middle layer, including additional amounts as 25 weight %, 30 weight %, 35 weight %, 40 weight %, 45 weight %, 50 weight %, 55 weight %, 60 weight %, 65 weight %, 70 weight %, and 75 weight % of the middle layer, and including any range of weight percentages derived from these values.

In some aspects, the middle layer comprises a matrix. In some embodiments, the matrix is a non-woven fabric.

In some embodiments, the matrix has a matrix water holding capacity (WHC) of from about 0.1 mg/cm$^2$ to about 10 mg/cm$^2$. The water holding capacity of the matrix means the amount of moisture the matrix can hold per 1 cm$^2$. Specifically, a 1 cm$^2$ matrix is prepared, and this is immersed in a solution (phosphate buffered saline containing 0.1% surfactant (Tween 80)) for a sufficiently long amount of time. Following this, the matrix is slowly pulled out of the solution for around five seconds, the weight of the sample before immersion measured in advance is subtracted from the weight of the sample holding the liquid, and then it is possible to determine the water holding capacity of the matrix per unit area (1 cm$^2$). In some embodiments, the matrix water holding capacity is from about 0.5 mg/cm$^2$ to about 8 mg/cm$^2$. In some embodiments, the matrix water holding capacity is from about 1 mg/cm$^2$ to about 6 mg/cm$^2$. In some embodiments, the matrix water holding capacity is from about 2 mg/cm$^2$ to about 5 mg/cm$^2$.

The water holding capacity of the matrix may be controlled by adjusting the thickness and weight of the matrix. It is preferable that the matrix has a thickness of 100 μm or less. In some embodiments, the matrix has a thickness in the range of about 10 μm to about 100 μm. In some embodiments, the matrix thickness is about 20 μm to about 90 μm. In some embodiments, the matrix thickness is about 30 μm to about 80 μm. In some embodiments, the matrix thickness is about 40 μm to about 60 μm.

In some embodiments, the matrix areal weight is about 10 g/m$^2$ to about 100 g/m$^2$. In some embodiments, the matrix areal weight is about 20 g/m$^2$ to about 80 g/m$^2$. In some embodiments, the matrix areal weight is about 30 g/m$^2$ to about 70 g/m$^2$. In some embodiments, the matrix areal weight is about 40 g/m$^2$ to about 60 g/m$^2$.

In some embodiments, the matrix areal weight is about 0.1 mg/cm$^2$ to about 30 mg/cm$^2$. In some embodiments, the matrix areal weight is about 5 mg/cm$^2$ to about 30 mg/cm$^2$. In some embodiments, the matrix areal weight is about 10 mg/cm$^2$ to about 30 mg/cm$^2$. In some embodiments, the matrix areal weight is about 20 mg/cm$^2$ to about 30 mg/cm$^2$. In some embodiments, the matrix areal weight is about 0.5 mg/cm$^2$ to about 5 mg/cm$^2$. In some embodiments, the matrix areal weight is about 0.5 mg/cm$^2$ to about 10 mg/cm$^2$.

In some embodiments, the size of the matrix is about 0.25 cm$^2$ to about 4 cm$^2$. In some embodiments, the size of the matrix is about 0.5 cm$^2$ to about 3 cm$^2$. In some embodiments, the size of the matrix is about 1 cm$^2$ to about 2 cm$^2$. In some embodiments, the size of the matrix is about 1 cm$^2$. In some embodiments, the size of the matrix is about 2 cm$^2$. In some embodiments, the size of the matrix is about 3 cm$^2$.

In some embodiments, the total amount of triptan and stabilizer per unit area of the matrix is 0.05 mg/cm$^2$ to 0.5 mg/cm$^2$. In some embodiments, the total amount of triptan and stabilizer per unit area of the matrix is 0.1 mg/cm$^2$ to 0.5 mg/cm$^2$. In some embodiments, the total amount of triptan and stabilizer per unit area of the matrix is 0.2 mg/cm$^2$ to 0.5 mg/cm$^2$. In some embodiments, the total amount of triptan and stabilizer per unit area of the matrix is 0.3 mg/cm$^2$ to 0.5 mg/cm$^2$. In some embodiments, the total amount of triptan and stabilizer per unit area of the matrix is 0.05 mg/cm$^2$ to 0.5 mg/cm$^2$.

In some embodiments, the pH of the matrix ingredients is from about 3 to about 6. In some embodiments, the pH of the matrix is from about 4 to about 6. In some embodiments, the pH of the matrix is from about 5 to about 6. In some embodiments, the pH of the matrix is about 3. In some embodiments, the pH of the matrix is about 4. In some embodiments, the pH of the matrix is about 5. In some embodiments, the pH of the matrix is about 6.

In some aspects, the matrix comprises from about 0.1 mg/cm$^2$ to about 5.0 mg/cm$^2$ triptan. In some embodiments, the matrix comprises from about 0.1 mg/cm$^2$ to about 3.0 mg/cm$^2$ triptan. In some embodiments, the matrix comprises from about 0.5 mg/cm$^2$ to about 5.0 mg/cm$^2$ triptan. In some embodiments, the matrix comprises from about 0.5 mg/cm$^2$ to about 3.0 mg/cm$^2$ triptan. In some embodiments, the matrix comprises from about 0.5 mg/cm$^2$ to about 2.0 mg/cm$^2$ triptan. In some embodiments, the matrix comprises about 0.5 mg/cm$^2$ triptan. In some embodiments, the matrix comprises about 1 mg/cm$^2$ triptan. In some embodiments, the matrix comprises about 2 mg/cm² triptan. In a preferred embodiment, the triptan is zolmitriptan.

In some aspects, the matrix comprises from about 0.1 mg/cm² to about 5.0 mg/cm² stabilizer. In some embodiments, the matrix comprises from about 0.1 mg/cm² to about 3.0 mg/cm² stabilizer. In some embodiments, the matrix comprises from about 0.5 mg/cm² to about 5.0 mg/cm² stabilizer. In some embodiments, the matrix comprises from about 0.5 mg/cm² to about 3.0 mg/cm² stabilizer. In some embodiments, the matrix comprises from about 0.5 mg/cm² to about 2.0 mg/cm² stabilizer. In some embodiments, the matrix comprises about 0.5 mg/cm² stabilizer. In some embodiments, the matrix comprises about 1 mg/cm² stabilizer. In some embodiments, the matrix comprises about 2 mg/cm² stabilizer. In a preferred embodiment, the stabilizer is sucrose.

In some aspects, the patch further comprises an anti-microbial agent. In some embodiments, the anti-microbial agent is selected from benzoic acid, methyl paraben, propyl paraben, benzalkonium chloride, chlorhexidine, cresol, salicylic acid, sorbic acid, benzetonium chloride and combinations thereof.

In some aspects, the present application also includes a method for using a patch as described herein to administer a triptan to a subject in need thereof. In some embodiments, a method of treating a subject comprises: identifying a subject having a migraine; opening a plurality of micropores in the skin of the subject; and applying the patch to the subject's skin over the micropores for a period of time. In some embodiments, the patch comprises a top layer comprising an adhesive, a middle layer comprising a triptan, and a bottom layer. In some embodiments, the bottom layer comprises a release liner. In some embodiments, the period of time is selected to deliver a therapeutically amount of the triptan through the plurality of micropores.

In some embodiments, the opening of the plurality of micropores in the skin of the subject comprises applying a transdermal microporation apparatus to the subject's skin. In some embodiments, the transdermal microporation apparatus comprises a conductive member comprising an array of conductive filaments. In some embodiments, the transdermal microporation apparatus comprises a conductive member comprising an array of conductive filaments. In some embodiments, the transdermal microporation opens the micropores by thermal tissue ablation. In some embodiments, the transdermal microporation creates micropores through the stratum corneum to the epidermis.

In some embodiments, the transdermal microporation apparatus has a poration energy in the range of from about 2 mJ/filament to about 8 mJ/filament. In some embodiments, the transdermal microporation apparatus has a filament density in the range of about 200 filaments/cm² to about 500 filaments/cm². In some embodiments, the transdermal microporation apparatus has a filament density of about 400 filaments/cm². In some embodiments, the transdermal microporation poration energy is about 4 mJ/filament to about 5 mJ. filament and the filament density is about 400 filaments/cm². In some embodiment, the transdermal microporation filament array size is in the range of from about 0.5 cm² to about 3 cm².

In some embodiments, the patch does not substantially irritate the subject's skin. As used herein, the term "does not substantially irritate a subject's skin" includes a resulting skin erythema score of about 3.0 or less, preferably about 2.0 or less, more preferably about 1.0 or less upon patch removal. In another embodiment, the conditions "does not substantially irritate a subject's skin" may refer to the skin irritation relief days of about 4.0 or less, preferably about 3.0 or less, more preferably about 2.5 or less. In another embodiment, the conditions "does not substantially irritate a subject's skin" if the resulting skin erythema score of about 3.0 or less, preferably about 2.0 or less, more preferably about 1.0 or less upon patch removal and the skin irritation relief days of about 4.0 or less, preferably about 3.0 or less, more preferably about 2.5 or less.

In some aspects, the present application also includes a system for using a patch to administer a triptan to a subject in need thereof. In some embodiments, the transdermal drug delivery patch system comprises: a transdermal microporation apparatus for heating a skin surface and a triptan drug delivery patch, including but not limited to a triptan drug delivery patch as described herein. In some embodiments, the drug delivery patch comprises a top layer comprising an adhesive; a middle layer that has at least one reservoir for containing a triptan; and a bottom layer, wherein the bottom layer comprises a release liner. In some embodiments, the microporation apparatus comprises a conductive member configured to generate heat energy based on a current flowing through the conductive member, and supplying the heat energy to the skin surface in contact with the conductive member during operation. In some embodiments, transdermal drug delivery patch system further comprises a power supply configured to provide a current to a conductive member in a plurality of pulses at a supply current value that is effective to open micropores in the skin surface.

EXAMPLES

Various embodiments and alternatives are disclosed in further detail in the following examples, which are not in any way intended to limit the scope of the claims. In the following, Zol=Zolmitriptan; CA=citric acid monohydrate; Suc=sucrose; AA=ascorbic acid; SB=sodium benzoate; TA=tartaric acid. A PASSPORT microporation system was utilized. The administration site was provided on the skin of the animal subjects by thermal poration using an apparatus having an array of 100 to 400 thermal poration filaments, such as the PassPort™ thermal poration system from Nitto Denko Corporation.

Zolmitriptan and Rizatriptan Benzoate were purchased from INKE S.A. (Spain). Sumatriptan Succinate was purchased from LGM Pharma (U.S.A.). The matrix of the drug patches used in Examples 1-10 were EH-1212 (Japan Vilene Company, LTD, Japan, WHC=4 mg/cm²) as a non-woven fabric material. This material is manufactured by thermal bonding two materials, white polyester fiber aggregates and transparent polyester film (12 micrometre) to make a consolidated sheet.

Example 1

Drug Patch Preparation

The drug patch of Examples 1-3 below were prepared according to the following method.

The patch was prepared according to the following method. First, a punching die was used to form a backing layer material of a predetermined size. For example, a 25×25 mm square. Next, a punching die was used to form a matrix material, for example, a non-woven fabric, into a predetermined size, for example, a 10×10 mm square. The formed matrix material was affixed to the center part of the backing layer material (hereinafter called blank patch). Next, an additive, such as, CA, AA, Suc, and the drug were weighed. Followed by a solution being added to the additive and drug.

The solutions used were deionized water or alcohol. Next, the solution was stirred until the additive and drug were completely dissolved, thereby preparing a drug solution. A mechanical pipette was used to drip the desired drug solution onto the matrix material area of the blank patch. The matrix material was dried at e.g. 60° C. in an oven for 20 to 50 minutes to form the patch structure. A release coating, such as a release liner, was coated on the patch structure. The completed patch was made into a pouch together with or without a drying agent by sealing with a heat sealer.

Animal Experiment: Transdermal Delivery by Microporation

Seventy-seven to 84 day old hairless guinea pigs were used as experimental animals. A drug patch was affixed on the flank side of the skin of the experimental animals that had undergone poration treatment under desired poration conditions. The filament density mainly affects the area to be utilized for the transfer of body fluid and ingredients in between skin and patch. The filament density was 200 or 400 filaments/cm$^2$, and the poration energy was about 4 and about 5 mJ/filament. The respective drug patches were each tested on each test subjects by applying the patch to a 1 cm$^2$ microporated administration site. During the period where the patch was affixed, and after it had adhered, blood was collected at a desired time, each medicinal component was extracted according to a conventional method. Next, the blood concentration was quantified by high performance liquid chromatography (LC-MS/MS). The given bioavailability of Tables 1-3 are relative bioavailability against subcutaneous injection.

Skin Irritation Score Criteria

A skin irritation examination was performed following the patch removal. The skin irritation examination scale was an assessment of the skin directly under the matrix. The skin irritation examination scale is presented in Table 1.

TABLE 1

| Skin Condition | Score |
| --- | --- |
| No erythema | 0 |
| Very slight erythema (barely perceptible) | 1 |
| Well-defined erythema | 2 |
| Moderate to severe erythema | 3 |
| Severe erythema (beet redness) to eschar formation | 4 |

This example describes the effects of skin irritation reducers and microporation conditions on triptan-induced skin irritation. The results are summarized in Table 2.

TABLE 2

| Exp. # | Microporation (+/−) | Dose | Bioavailability (±SE %) | Skin Irritation Score (±SD) | Skin Irritation Relief Days (±SD) |
| --- | --- | --- | --- | --- | --- |
| 1-1 | − | 2 mg Zol and CA (1:1 eq.)) (2 times appl.: 1$^{st}$ 24 h, 2$^{nd}$ 6 h) | N/A | 0 ± 0.0 | 0 ± 0.0 |
| 1-2 | + | 2 mg Zol (2 mg Zol, 1.96 mg Suc, 0.1 mg SB) | N/A | 2.8 ± 0.5 | 4.5 ± 1.0 |
| 1-3 | + | 2 mg Zol and AA (1:1 eq.) | 89.6 ± 4.5 | 3.3 ± 0.3 | 3.8 ± 1.4 |
| 1-4 | + | 2 mg Zol and CA (1:1 eq.)) | 64.8 ± 10.2 | 1.8 ± 0.5 | 1.3 ± 0.8 |
| 1-5 | + | 2 mg Zol and TA (1:1 eq.)) | 96.0 ± 11.1 | 2.6 ± 0.5 | 1.8 ± 0.2 |

Example 2

This examples describes the effects of skin irritation reducers and microporation conditions on triptan-induced skin irritation. The results are summarized in Table 3.

TABLE 3

| Exp. # | Microporation (+/−) | Dose | Bioavailability (+SE %) | Skin Irritation Score (±SD) | Skin Irritation Relief Days (±SD) |
| --- | --- | --- | --- | --- | --- |
| 2-1 | − | 2 mg Zol (2 mg Zol, 1.96 mg Sue, 0.1 mg SB) | No Data | 2.8 ± 0.5 | 4.5 ± 1.0 |
| 2-2 | + | 2 mg Zol and CA (1:0.5 eq.) | 82.3 ± 3.6% | 2.8 ± 0.4 | 2.1 ± 0.7 |
| 2-3 | + | 2 mg Zol and CA (1:0.75 eq.) | 72.3 ± 2.1% | 2.8 ± 0.3 | 1.4 ± 0.4 |
| 2-4 | + | 2 mg Zol and CA (1:1 eq.) | 84.0 ± 9.3% | 2.4 ± 0.4 | 1.4 ± 0.5 |
| 2-5 | + | 2 mg Zol and CA (1:1.5 eq.) | 76.2 ± 5.1% | 2.0 ± 0.4 | 1.6 ± 0.9 |
| 2-6 | + | 2 mg Zol and CA (1:2 eq.) | 69.9 ± 5.0% | 1.6 ± 0.2 | 2.3 ± 0.4 |

TABLE 3-continued

| Exp. # | Microporation (+/−) | Dose | Bioavailability (+SE %) | Skin Irritation Score (±SD) | Skin Irritation Relief Days (±SD) |
|---|---|---|---|---|---|
| 2-7 | + | 2 mg Zol and CA (1:3 eq.) | 61.2 ± 6.7% | 1.8 ± 0.3 | 5.8 ± 1.1 |

Example 3

This examples describes the effects of skin irritation reducers and microporation conditions on triptan-induced skin irritation. The results are summarized in Table 4.

TABLE 4

| Exp. # | Microporation (+/−) | Dose | Bioavailability (+SE %) | Skin Irritation Score (±SD) |
|---|---|---|---|---|
| 3-1 | + (200 pores) | 6 mg Sumatriptan Succinate and AA (Sum: (AA + SA) = 1:1.2 eq.) | 76.7% | 1.0 ± 0.0 |
| 3-2 | + (200 pores) | 6.54 mg Rizatriptan Benzoate and AA (Riz: (AA + BA) = 1:1.2 eq.) | 28.0% | 1.0 + 0.7 |

Example 4

This example describes an administration route study in hairless rats. In this study, four groups of hairless rats were tested under the following conditions: (1) Group 1 (2 mg zolmitriptan, oral administration); (2) Group 2 (2 mg zolmitriptan, intranasal administration; (3) Group 3 (2 mg zolmitriptan, intravenous injection); and (4) Group 4 (2 mg zolmitriptan, transdermal microporation). The results are summarized in FIG. 1 and Table 5.

Animal Experiment: Oral Administration, Group 1

Hairless rats were used as experimental animals. After oral administration of an drug solution (2.0 ml) containing 2.0 mg of zolmitriptan, blood was collected at a desired time, each medicinal component was extracted according to a conventional method, then blood concentration was quantified by high performance liquid chromatography (LC-MS/MS).

Animal Experiment: Intranasal Administration, Group 2

Hairless rats were used as experimental animals. After intravenous administration of an drug solution (10 μl) containing 2 mg of zolmitriptan, blood was collected at a desired time, each medicinal component was extracted according to a conventional method, then blood concentration was quantified by high performance liquid chromatography (LC-MS/MS).

Animal Experiment: Intravenous Administration, Group 3

Hairless rats were used as experimental animals. After intravenous administration of an drug solution (200 μl) containing 2 mg of zolmitriptan, blood was collected at a desired time, each medicinal component was extracted according to a conventional method, then blood concentration was quantified by high performance liquid chromatography (LC-MS/MS).

Animal Experiment: Transdermal Delivery by Microporation, Group 4

Hairless rats were used as experimental animals. A drug patch was affixed on the flank side of skin of experimental animals that had undergone microporation treatment under the desired conditions. In this study, microporation condition of transdermal microporation was 400 pores/$cm^2$, 5.2 mJ/filament. The administration side was 1 $cm^2$. During the period where the patch was affixed, and after it had adhered, blood was collected at a desired time, each medicinal component was extracted according to a conventional method, then blood concentration was quantified by high performance liquid chromatography (LC-MS/MS). A Patch formulation of this study was 2 mg Zolmitriptan, sucrose 0.5 mg, AA 4 mg, 1 $cm^2$ non-woven matrix (EH-1212, WHC=4 mg/$cm^2$), The given bioavailability of Table 5 is absolute bioavailability against IV injection.

TABLE 5

| Group | AUC (ng/ml*hr) | BA (%) | Cmax (ng/mL) | Tmax (hr) |
|---|---|---|---|---|
| 1 | 227.43 | 11.4 | 74 | 4.50 |
| 2 | 239.33 | 12.0 | 127 | 2.25 |
| 3 | 1997.10 | 100.0 | 5025 | 0.05 |
| 4 | 1426 | 71.4 | 577 | 0.63 |

Example 5

This example describes an administration route study in guinea pigs using the same method mentioned in Example 4. In this study, base refers to Zomitriptan. Poration condition of transdermal microporation and the matrix of the drug patch was same as the Group 4 of Example 4.

Figure 2:
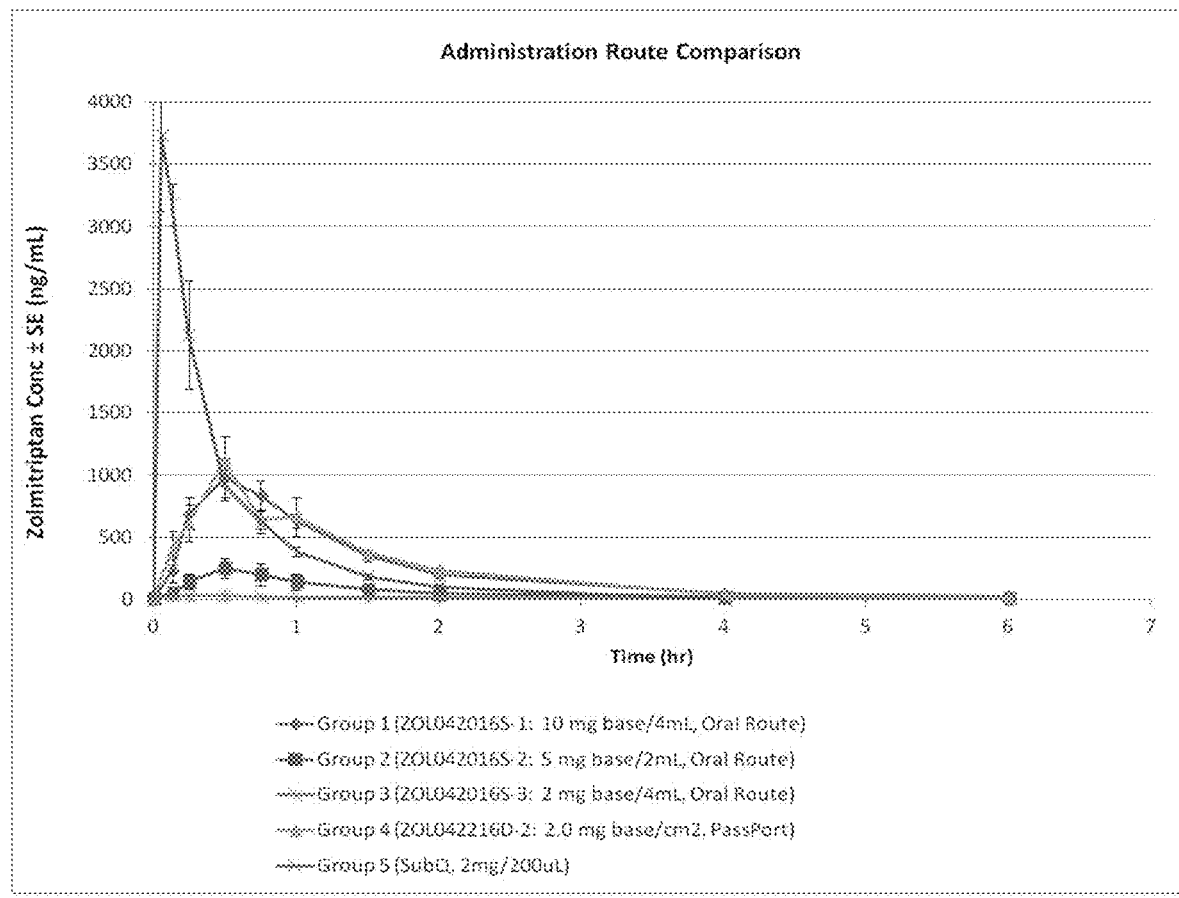
FIG. 2 illustrates the results of an administration route comparison study in guinea pigs.

In this study, five groups of guinea pigs were tested under the following conditions: (1) Group 1 (10 mg base/4 ml, oral route); (2) Group 2 (5 mg base/2 ml, oral route); (3) Group 3 (2 mg base/4 mL, oral route); (4) Group 4 (2.0 mg base/$cm^2$, transdermal microporation); and (5) Group 5 (2 mg/200 μL, SubQ). The results are summarized in FIG. 2 and Table 6. The given bioavailability of Tables 6 is relative bioavailability against subcutaneous injection.

Figure 3:
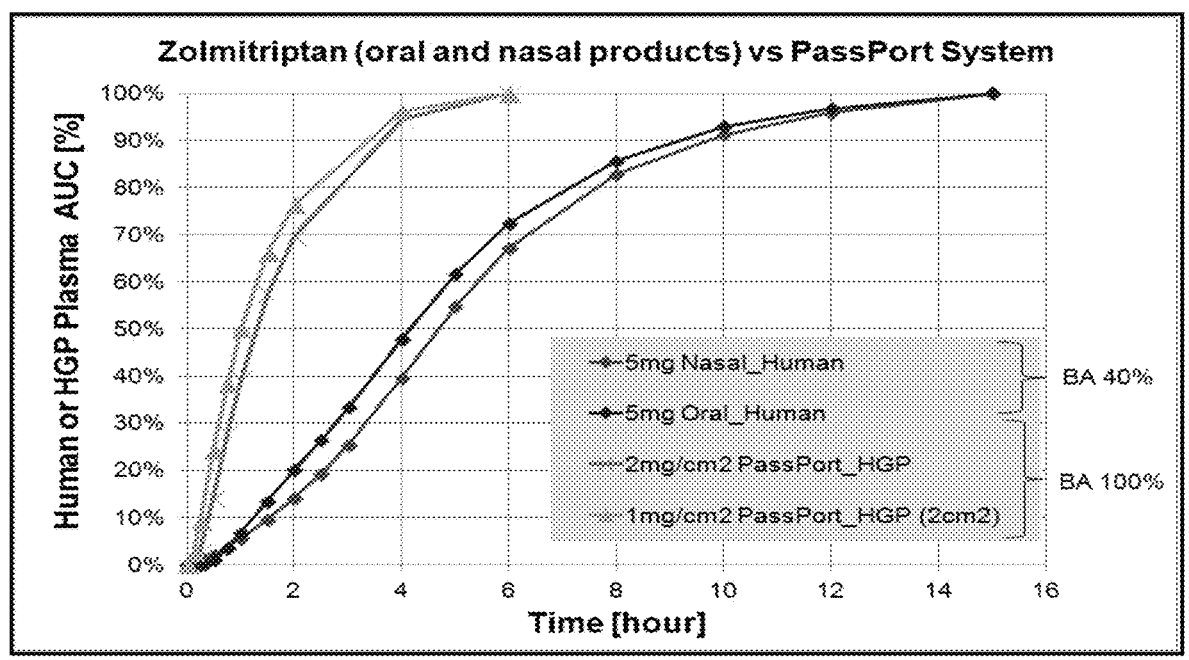
FIG. 3 illustrates a comparison of data for humans and hairless guinea pigs.

In a further study, a PK study was conducted comparing humans to hairless guinea pigs (HGP). The results are summarized in FIG. 3 (Headache 2006, 46, 138-149).

TABLE 6

| Group | AUC (ng/ml*hr) | BA (%) | Cmax (ng/mL) | Tmax (hr) |
|---|---|---|---|---|
| 1 | 1387 | 16.2 | 910 | 0.44 |
| 2 | 353 | 8.3 | 259 | 0.56 |
| 3 | 77 | 4.5 | 25 | 0.33 |
| 4 | 1439 | 84.2 | 864 | 0.50 |
| 5 | 1709 | 100.0 | 3878 | 0.09 |

Example 6

This example describes various stabilizers and skin irritation reducers with microporation. The matrix is the same as above. Briefly, the microporation condition of transdermal microporation as follows; the pore density was 400 pores/cm$^2$, the poration energy was 4 mJ/filament and the filament density was 400 filament/cm$^2$. The administration site was 1 cm$^2$. The results are summarized in Tables 7-11. Table 7 describes citric acid amount study with microporation using guinea pigs. The given bioavailability of Tables 7-10 is relative bioavailability against subcutaneous injection.

TABLE 7

| Composition | Gr. 1-1 | Gr. 1-2 | Gr. 1-3 | Gr. 1-4 | Gr. 1-5 |
|---|---|---|---|---|---|
| Dosage | Transdermal microporation | | | | |
| Zolmitriptan (mg) | 2.00 | 2.00 | 2.00 | 2.00 | 2.00 |
| Sucrose (mg) | 0.50 | 0.50 | 0.50 | 0.50 | 0.50 |
| Citric acid monohydrate (mg) (Molar equivalent to zolmitriptan) | 0.73 (0.5 eq.) | 1.10 (0.75 eq.) | 1.46 (1 eq.) | 2.19 (1.5 eq.) | 2.93 (2 eq.) |
| Sodium benzoate (mg) | 0.15 | 0.15 | 0.15 | 0.15 | 0.15 |
| Tmax (hours) | 0.7 | 0.7 | 0.8 | 0.9 | 0.9 |
| Bioavailability | 82% | 72% | 84% | 76% | 70% |
| Skin irritation (Just after patch removal) | 2.8 | 2.8 | 2.4 | 2.0 | 1.6 |
| Skin irritation relief (Days to recover to score 1) | 2.1 | 1.4 | 1.4 | 1.6 | 2.3 |

Table 8 summarizes results of a study using organic acids as skin irritation reducers with microporation on guinea pigs.

TABLE 8

| Composition | Gr. 1-3 | Gr. 2-1 | Gr. 2-2 |
|---|---|---|---|
| Dosage | Transdermal microporation | | |
| Zolmitriptan (mg) | 2.00 | 2.00 | 2.00 |
| Sucrose (mg) | 0.50 | 0.50 | 0.50 |
| Acid species | Citric acid monohydrate | Ascorbic acid | Tartaric acid |
| Acid (1 eq.) | 1.46 | 1.23 | 1.04 |
| Sodium benzoate (mg) | 0.15 | 0.15 | 0.15 |
| Tmax (hours) | 0.8 | 0.8 | 0.7 |
| Bioavailability | 84% | 90% | 96% |
| Skin irritation (Just after patch removal) | 2.4 | 3.3 | 2.6 |
| Skin irritation relief (Days to recover to score 1) | 1.4 | 3.8 | 1.8 |

Table 9 describes summarizes results of a study using a stabilizer, sucrose, and microporation on guinea pigs.

TABLE 9

| Composition | Gr. 3-1 | Gr. 3-2 | Gr. 3-3 | Gr. 3-4 | Gr. 3-5 | Gr. 3-6 |
|---|---|---|---|---|---|---|
| Dosage | Transdermal microporation | | | | | |
| Zolmitriptan (mg) | 2.00 | 2.00 | 2.00 | 2.00 | 2.00 | 2.00 |
| Sucrose (mg) | 0.50 | 0.30 | 0.20 | 0.10 | 0.05 | none |
| Citric acid monohydrate (mg) (Molar equivalent to zolmitriptan) | 1.46 (1 eq.) | 1.46 (1 eq.) | 1.46 (1 eq.) | 1.46 (1 eq.) | 1.46 (1 eq.) | 1.46 (1 eq.) |
| Sodium benzoate (mg) | 0.15 | 0.15 | 0.15 | 0.15 | 0.15 | 0.15 |
| Appearance (50 C., 3-month) | No color change | No color change | No color change | Slightly Yellow | Slightly Yellow | Yellow |

Table 10 summarizes results of a study using zolmitriptan with microporation on guinea pigs.

TABLE 10

| Composition | Gr. 4-1 | Gr. 4-2 | Gr. 4-3 | Gr. 4-4 | Gr. 4-5 |
|---|---|---|---|---|---|
| Dosage | Transdermal microporation | | | | |
| Zolmitriptan (mg) | 0.50 | 2.00 | 3.00 | 4.00 | 4.00 |
| Sucrose (mg) | 0.50 | 0.50 | 0.50 | 0.50 | 0.50 |
| Citric acid monohydrate (1 eq.) | 0.37 | 1.46 | 2.19 | 2.93 | 2.93 |
| Sodium benzoate | 0.10 | 0.10 | 0.10 | 0.15 | 0.15 |
| Poration Area (cm$^2$) | 1.0 | 1.0 | 1.0 | 1.5 | 2.0 |
| Zolmitriptan conc. (mg/cm$^2$) | 0.5 | 2.0 | 3.0 | 2.7 | 2.0 |
| AUC (hr*ng/mL) | 364 | 2103 | 2347 | 3661 | 4312 |
| Skin irritation (Just after patch removal) | 1.6 | 2.1 | 2.0 | 2.1 | 2.0 |

Table 11 summarizes the results of a dosage comparison study using hairless rats

TABLE 11

| Composition | Gr. 5-1 | Gr. 5-2 | Gr. 5-3 | Gr. 5-4 | Gr. 5-5 | Gr. 5-6 | Gr. 5-7 |
|---|---|---|---|---|---|---|---|
| Dosage (Route) | Transdermal microporation | Oral | Oral | Oral | Nasal | Nasal | Nasal |
| Zolmitriptan | 2.00 | 10.00 | 5.00 | 2.00 | 10.00 | 5.00 | 2.00 |
| Sucrose | 0.50 | — | — | — | — | — | — |
| Citric acid monohydrate | 1 eq. | 1 eq. | 1 eq. | 1 eq. | 1 eq. | 1 eq. | 1 eq. |
| Sodium benzoate | — | — | — | — | — | — | — |
| Sodium phosphate dibasic | — | 4.94 | 2.47 | 0.99 | — | — | — |
| AUC (hr*ng/mL) | 1426 | 1707 | 843 | 227 | 818 | 419 | 239 |
| Cmax (ng/mL) | 577 | 530 | 242 | 74 | 424 | 132 | 127 |
| Tmax (hours) | 0.6 | 4.0 | 3.3 | 4.5 | 3.2 | 3.1 | 2.3 |
| Bioavailability (%) | 71% | 17% | 17% | 11% | 8% | 8% | 12% |

The given bioavailability of Table 11 is absolute bioavailability against IV injection.

Example 7

This example describes various effects of filament density. To investigate the effect of filament density on PK profile and side effects (pain by poration and skin irritation), these studies were conducted. The filament density mainly affects the area to be utilized for the transfer of body fluid and ingredients in between skin and patch. The range of filament density was 100 filaments/cm$^2$ to 400 filaments/cm$^2$, and the poration energy was from 3 to 4 mJ/filament. The detailed conditions are summarized in the Table 12.

TABLE 12

| Condition | | #1 | #2 | #3 | #4 | #5 | #6 |
|---|---|---|---|---|---|---|---|
| Poration condition | Area (cm$^2$) | 1.0 | 1.0 | 1.0 | 1.0 | 1.0 | 1.0 |
| | Density (filaments/cm$^2$) | 100 | 200 | 400 | 100 | 200 | 400 |
| | Energy (mJ/filament) | 3 | 3 | 3 | 4 | 4 | 4 |
| Formulation (mg/patch) | Zolmitriptan | 2.00 | 2.00 | 2.00 | 2.00 | 2.00 | 2.00 |
| | Sucrose | 0.50 | 0.50 | 0.50 | 0.50 | 0.50 | 0.50 |
| | Citric acid monohydrate | 1.46 | 1.46 | 1.46 | 1.46 | 1.46 | 1.46 |
| | Sodium benzoate | 0.10 | 0.10 | 0.10 | 0.10 | 0.10 | 0.10 |
| Animal study information | ID (AZOL) | 0049 | 0048 | 0049 | 0049 | 0048 | 0049 |
| | Group | 5 | 2 | 2 | 4 | 1 | 1 |

Figure 4:
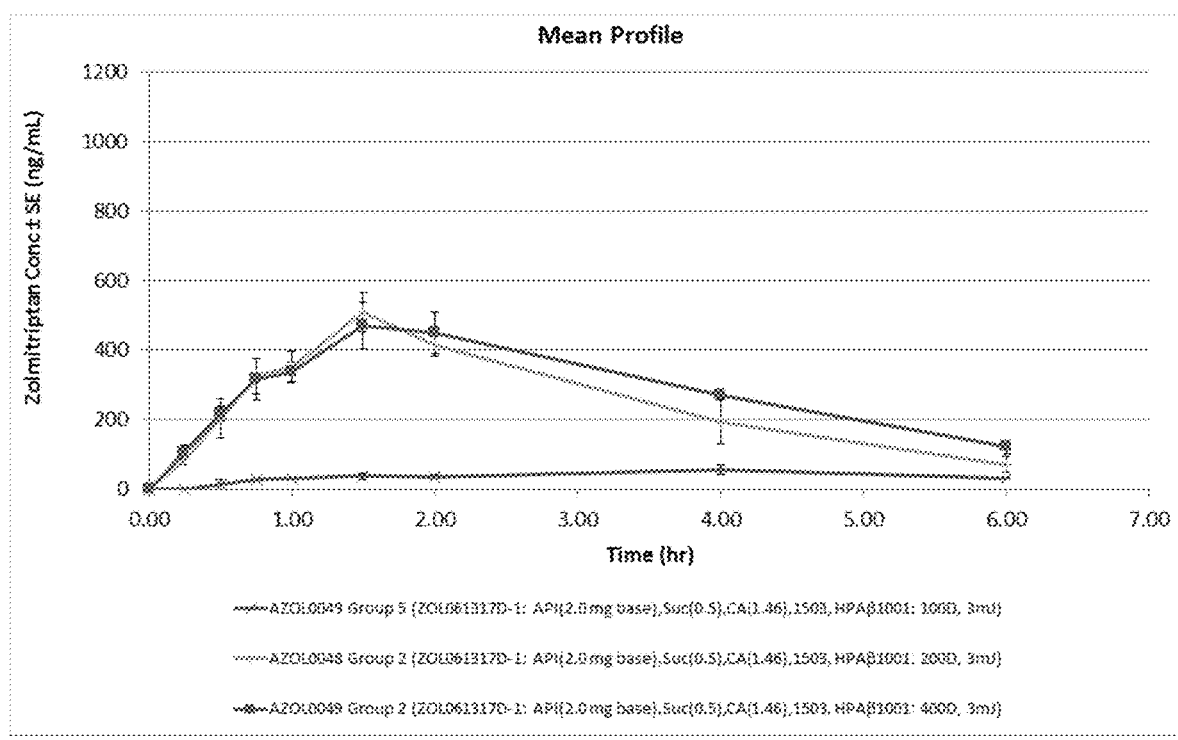
FIG. 4 illustrates pharmacokinetic (PK) profiles for different filament densities
Figure 5:
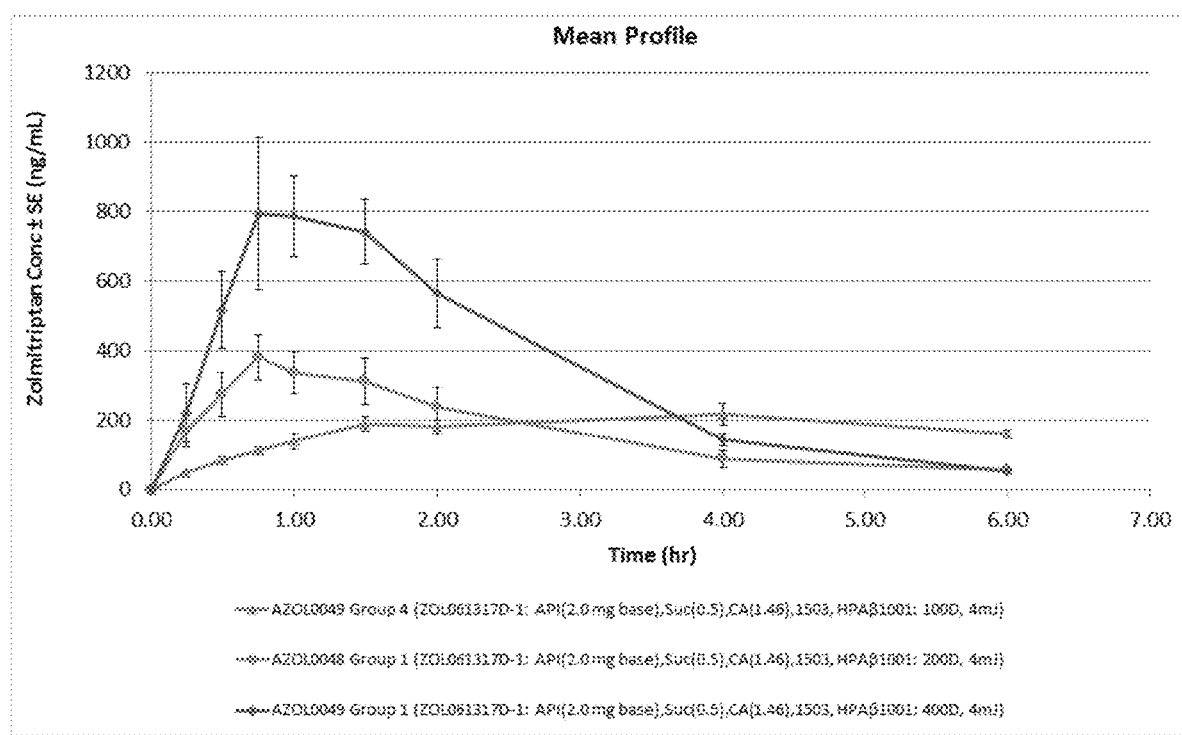
FIG. 5 illustrates PK profiles for different filament densities.
Figure 6:
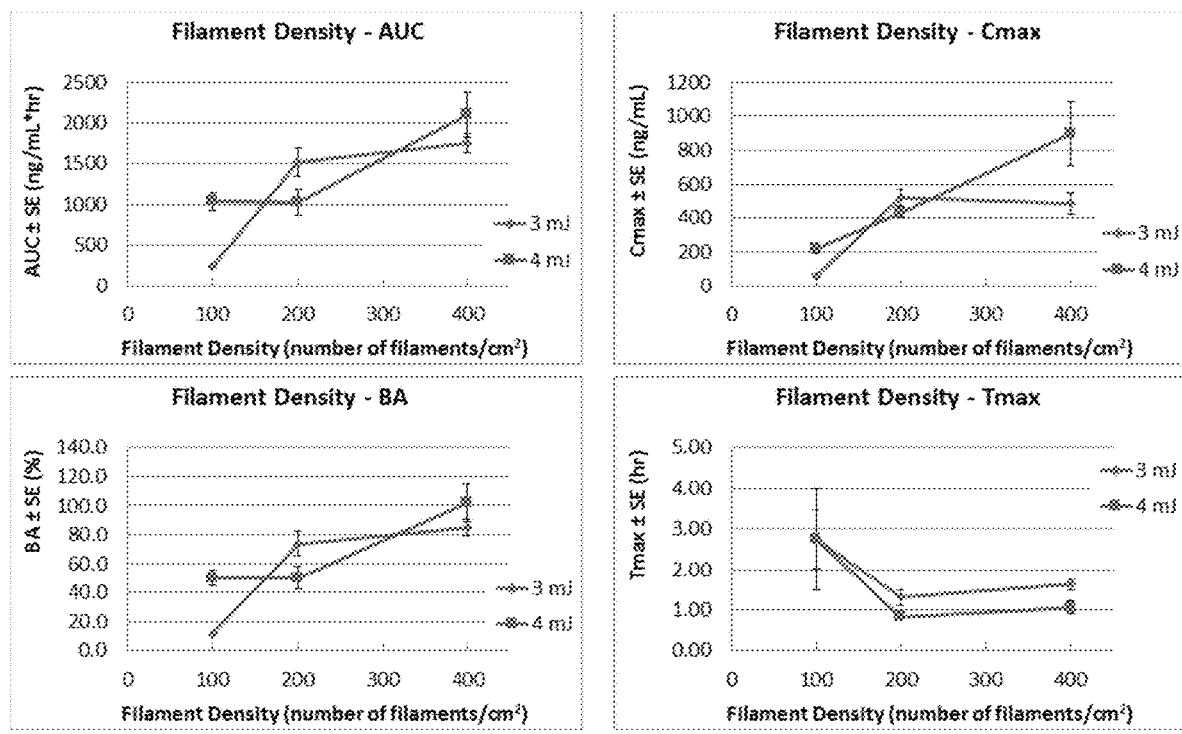
FIG. 6 illustrates relationships between filament density and PK results.

As for the results of PK profiles, a density of 100 filaments/cm$^2$ showed lower Cmax and slower Tmax, which means the profile is a kind of sustained release shape (See FIGS. 4 and 5). This indicates a density of 100 filaments/cm$^2$ density was slower to deliver drug into systemic circulation. On the other hand, higher densities resulted in the higher Cmax and faster Tmax. Especially, a density of 400 filaments/cm$^2$ with 4 mJ energy demonstrated the highest Cmax and the fastest Tmax in the tested groups. Additionally, the relative BA of the condition was about 100%. It appears that a density of 400 filaments/cm$^2$ is an excellent candidate under the tested conditions to create enough area to obtain body fluid for dissolving ingredients then deliver the triptan drug. The PK data is summarized in the FIG. 6 and Table 13.

TABLE 13

| Evaluation item | Target criteria | Result (±SE) | | | | | |
|---|---|---|---|---|---|---|---|
| | | #1 | #2 | #3 | #4 | #5 | #6 |
| Density (filaments/cm$^2$) | — | 100 | 200 | 400 | 100 | 200 | 400 |
| Energy (mJ/filament) | | 3 | 3 | 3 | 4 | 4 | 4 |
| n (for PK) | — | 2 | 4 | 4 | 4 | 4 | 4 |
| AUC ± SE (hr*ng/mL) | 2252 | 238 ± 13 | 1521 ± 177 | 1752 ± 116 | 1035 ± 113 | 1028 ± 159 | 2103 ± 275 |
| Cmax ± SE (ng/mL) | 768 | 60 ± 13 | 520 ± 51 | 487 ± 63 | 222 ± 30 | 423 ± 30 | 896 ± 191 |
| Tmax ± SE (hours) | 2.0 | 2.75 ± 1.25 | 1.31 ± 0.19 | 1.63 ± 0.13 | 2.75 ± 0.72 | 0.81 ± 0.06 | 1.06 ± 0.16 |
| Bioavailability ± SE (%) | — | 11.5 ± 0.6 | 73.8 ± 8.6 | 85.0 ± 5.6 | 50.3 ± 5.5 | 49.9 ± 7.7 | 102.1 ± 13.3 |
| Pain by poration ± SD | — | 0.0 ± 0.0 | 0.6 ± 0.5 | 0.5 ± 0.6 | 0.8 ± 1.0 | 1.8 ± 0.4 | 1.8 ± 0.5 |
| Skin irritation ± SD (Just after patch removal) | ≤2 | 0.8 ± 0.3 | 2.2 ± 0.4 | 1.9 ± 0.3 | 1.6 ± 0.3 | 2.1 ± 0.7 | 2.1 ± 0.3 |

TABLE 13-continued

| Evaluation item | Target criteria | Result (±SE) | | | | | |
|---|---|---|---|---|---|---|---|
| | | # 1 | # 2 | # 3 | # 4 | # 5 | # 6 |
| Skin irritation relief ± SD (Days to recover to score 1) | — | 0.0 ± 0.0 | 1.8 ± 0.8 | 2.8 ± 1.3 | 1.8 ± 0.5 | 3.0 ± 1.9 | 3.2 ± 0.8 |

Figure 7:
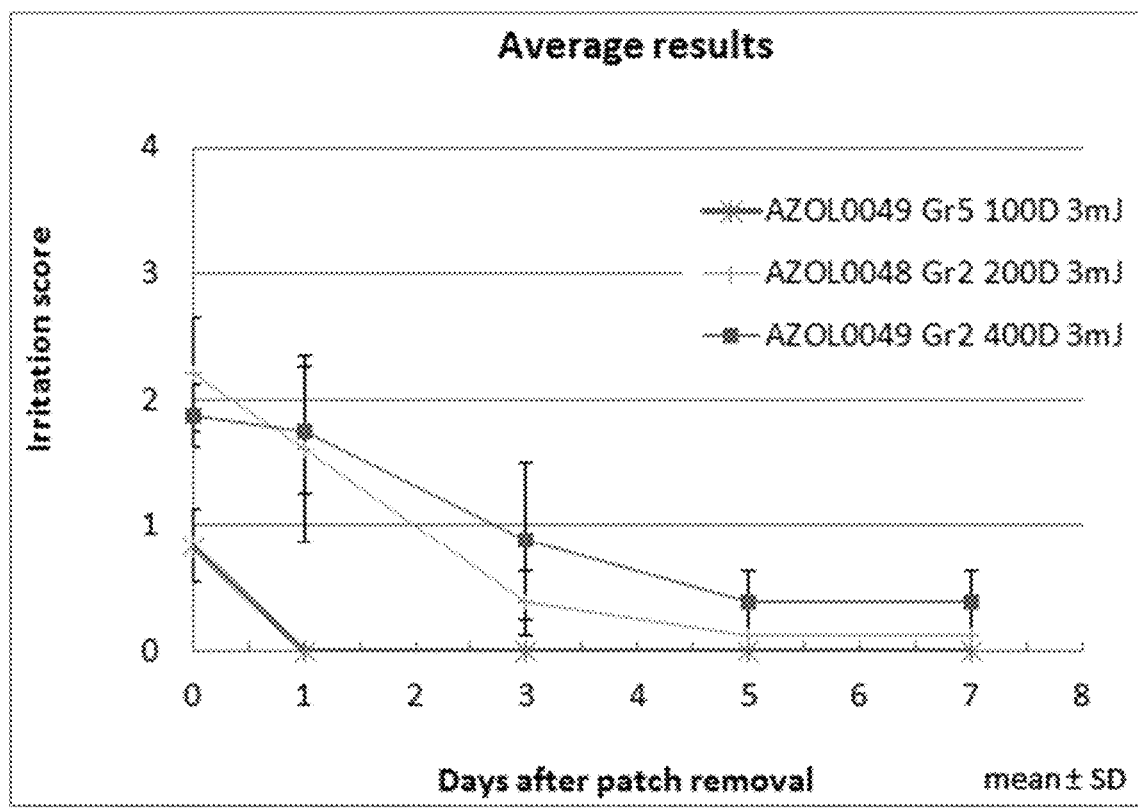
FIG. 7 illustrates skin irritation results for different filament densities.
Figure 8:
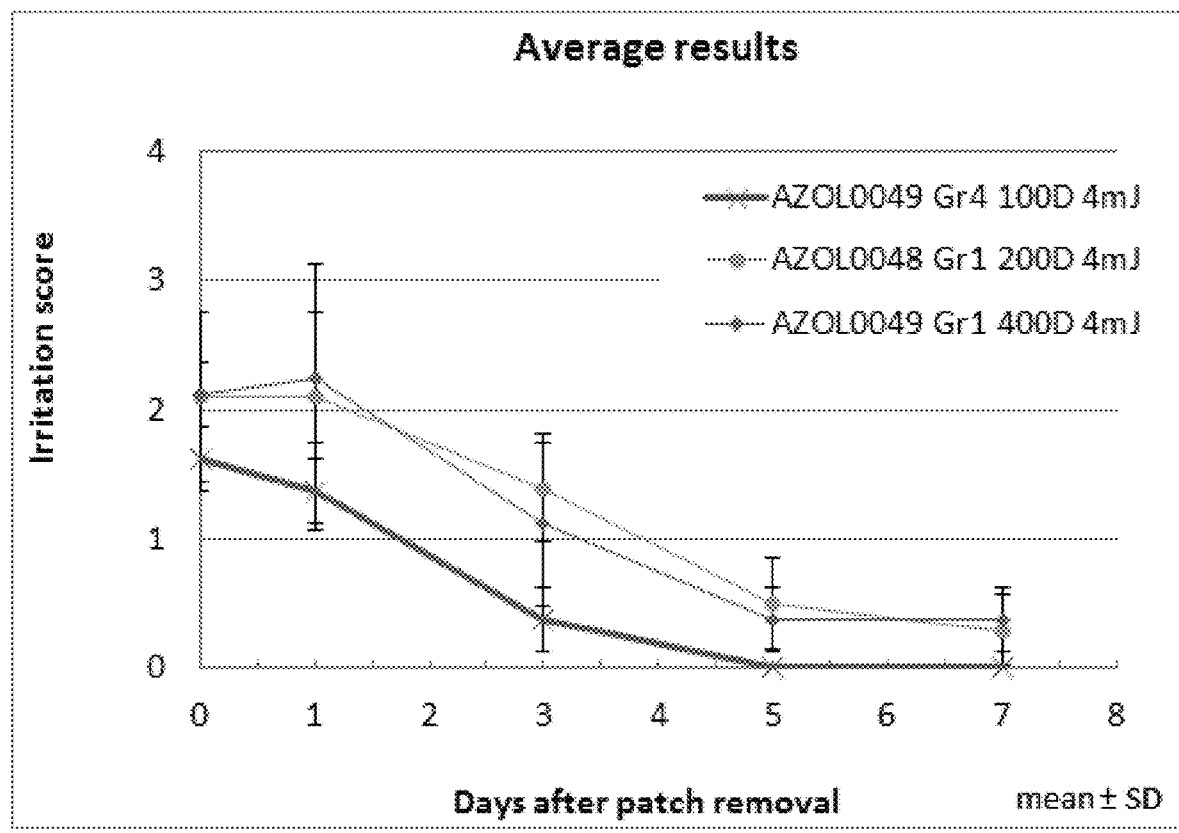
FIG. 8 illustrates skin irritation results for different filament densities.
Figure 9:
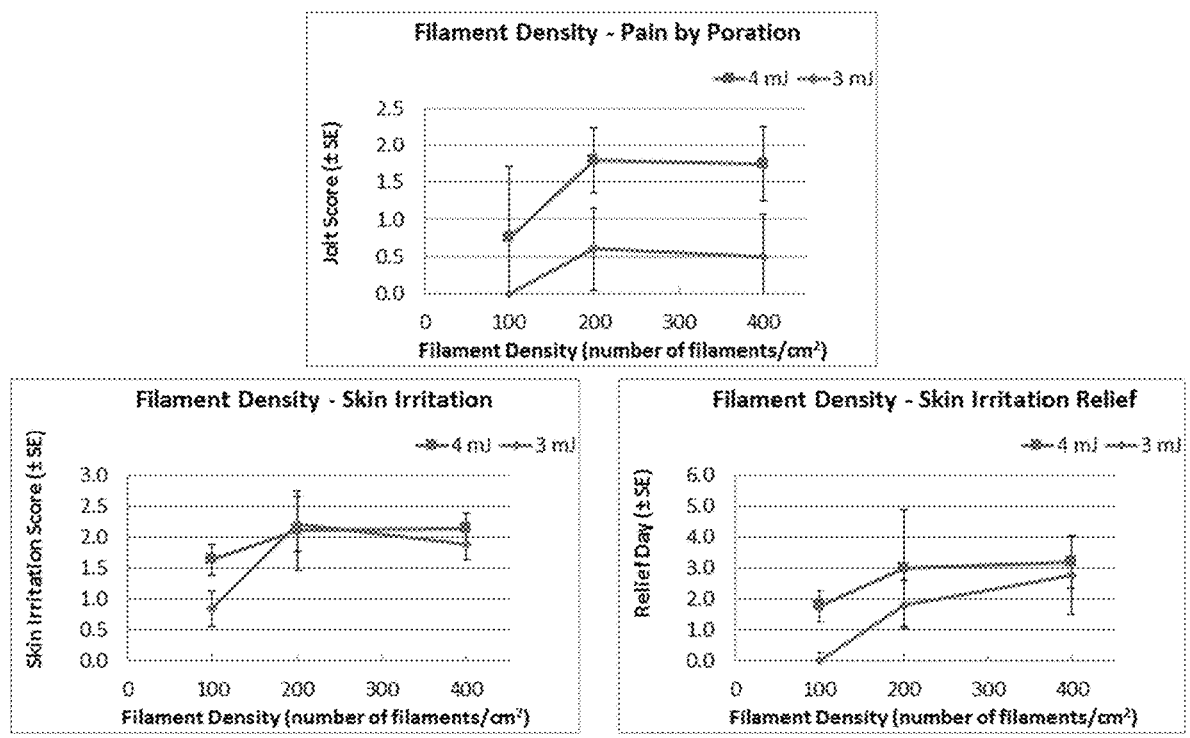
FIG. 9 illustrates relationships between filament density and side effects.

From the perspective of side effects, 100 filaments/cm$^2$ density was the mildest condition on both pain by poration and skin irritation, which is reasonable (FIG. 7, 8, 9). Comparing 200 filaments/cm$^2$ density and 400 filaments/cm$^2$ density, significant differences were not observed, and both conditions did not cause severe side effects.

The given bioavailability of Table 13 is relative bioavailability against SC injection.

Example 8

This example describes various effects to heating energy. The poration energy is related to the pore shape such as depth and width. In these animal studies, 2 to 5 mJ/filament poration energy for 400 filaments/cm$^2$ density was utilized, as shown in the Table 14.

TABLE 14

| | Conditions | # 1 | # 2 | # 3 | # 4 |
|---|---|---|---|---|---|
| Poration condition | Area (cm$^2$) | 1.0 | 1.0 | 1.0 | 1.0 |
| | Density (filaments/cm$^2$) | 400 | 400 | 400 | 400 |
| | Energy (mJ/filament) | 2 | 3 | 4 | 5 |
| Formulation (mg/patch) | Zolmitriptan | 2.00 | 2.00 | 2.00 | 2.00 |
| | Sucrose | 0.50 | 0.50 | 0.50 | 0.50 |
| | Citric acid monohydrate | 1.46 | 1.46 | 1.46 | 1.46 |
| | Sodium benzoate | 0.10 | 0.10 | 0.10 | 0.15 |
| Animal study information | ID (AZOL) | 0049 | 0049 | 0049 | 0050 |
| | Group | 3 | 2 | 1 | 1 |

Figure 10:
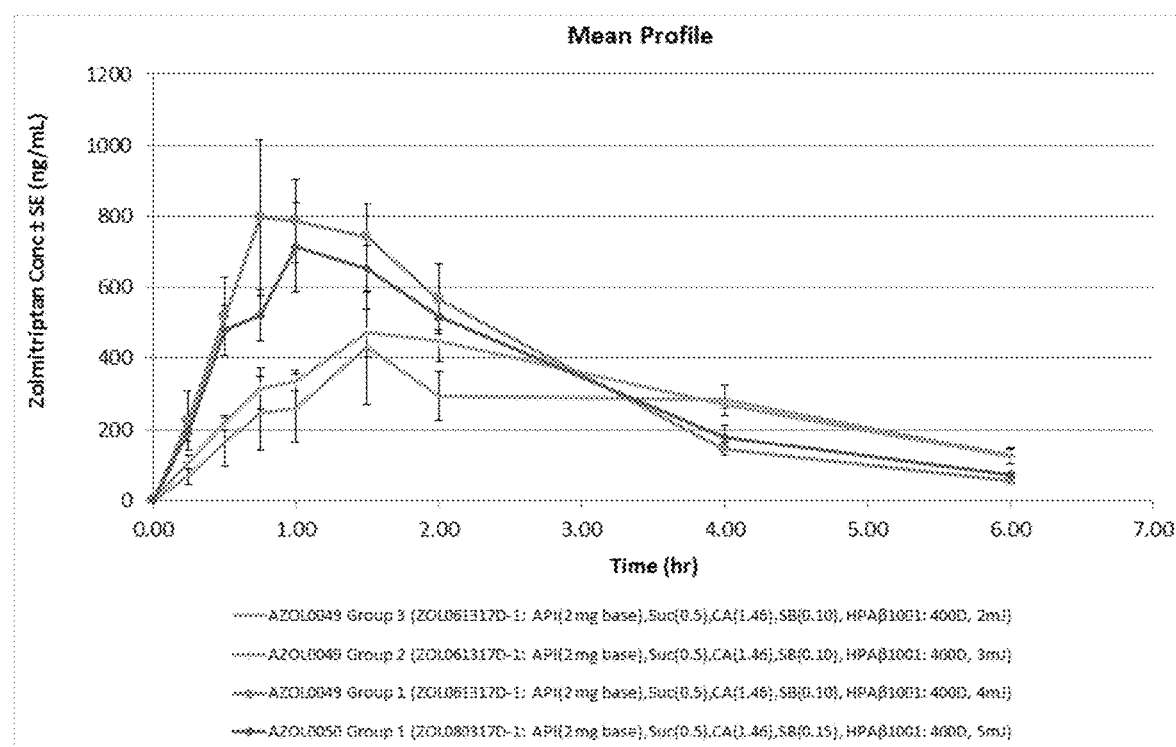
FIG. 10 illustrates PK profiles for different poration energies.
Figure 11:
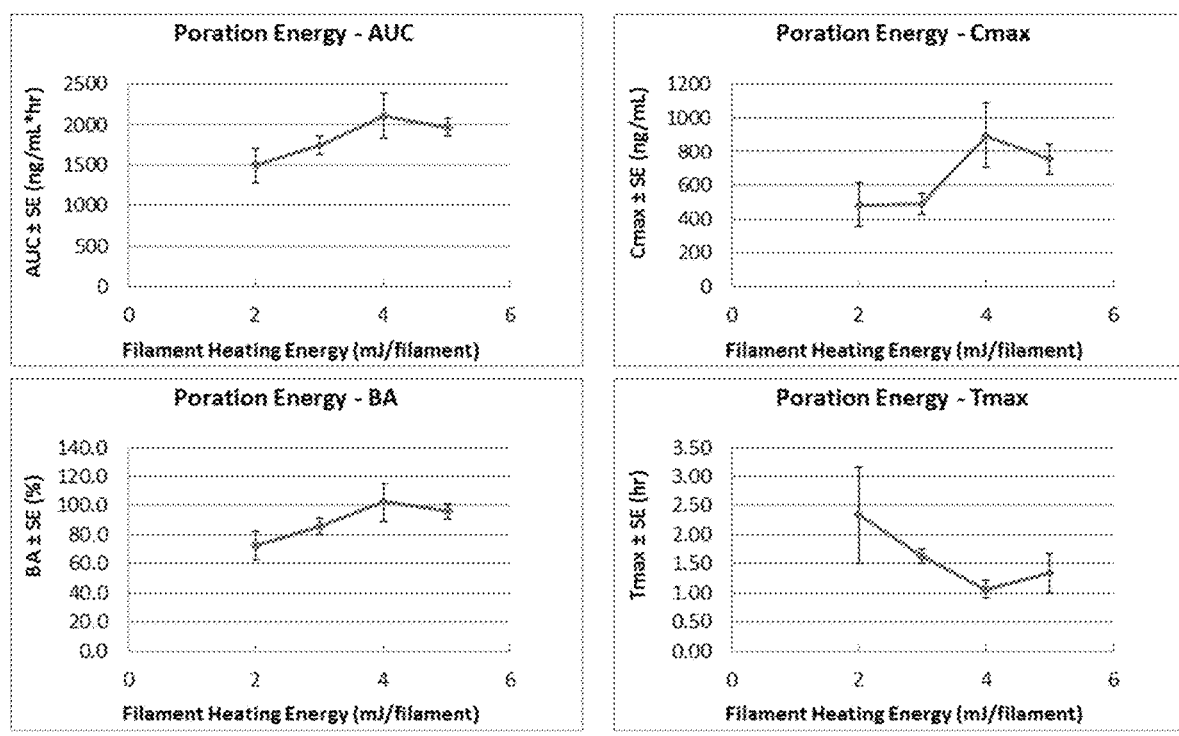
FIG. 11 illustrates relationships between poration energy and PK results.

As the result of PK studies, all the evaluated data (AUC, BA, Cmax, and Tmax) showed almost proportional trend in the range of 2 to 4 mJ/filament, and the 4 mJ/filament was the most desirable condition in any evaluation items (see FIGS. 10 and 11). However, in comparison of 4 and 5 mJ/filament, the PK results of 5 mJ/filament was almost same or even a little bit worse than the results of 4 mJ/filament. This implies 5 mJ/filament creates larger pores than required and induces more body fluid than needed for 2 mg dose formulation. In other words, the drug concentration in body fluid induced by 5 mJ/filament energy may be lower than the one by 4 mJ/filament in the case of 2 mg dose formulation. Therefore, the osmotic pressure and diffusion of drug with 5 mJ/filament is also lower than the ones with 4 mJ/filament. That is why 400 filaments/cm$^2$ filament density with 4 mJ/filament poration energy is an excellent condition for 2 mg dosage form.

Figure 12:
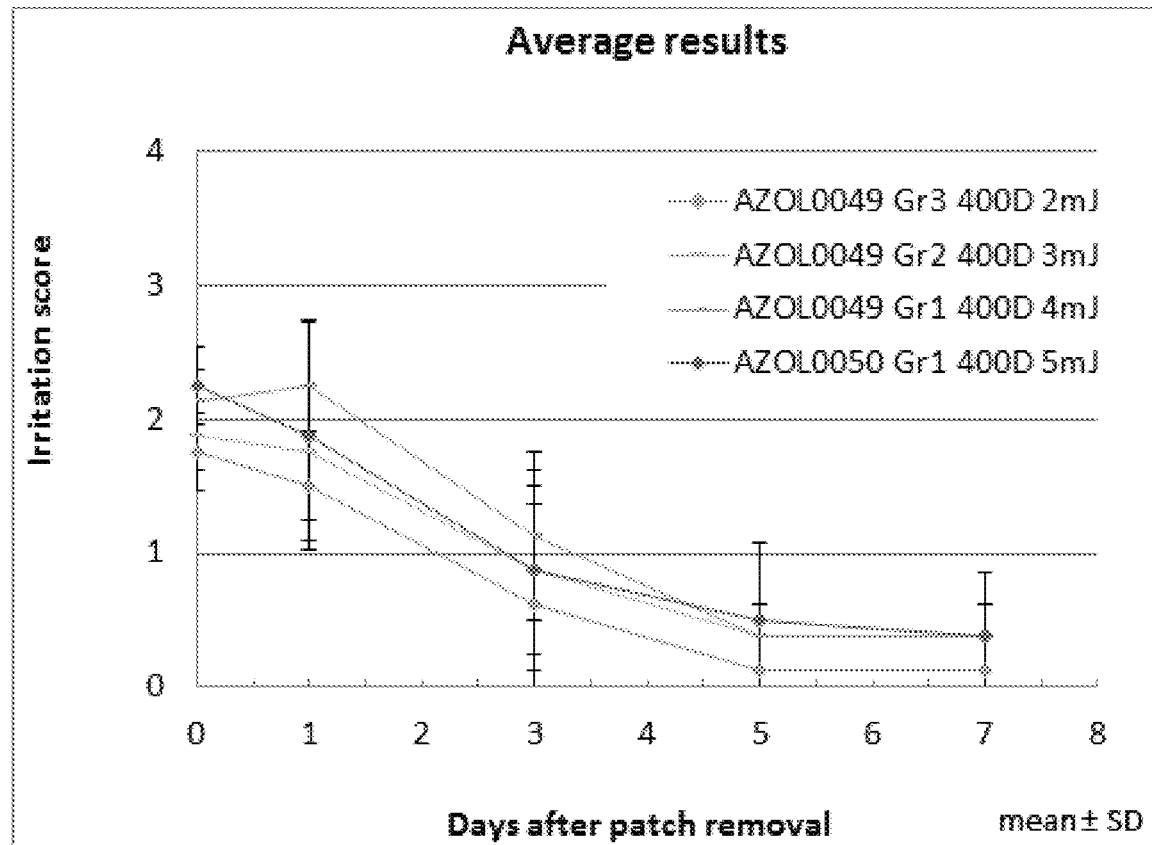
FIG. 12 illustrates skin irritation results for different poration energies.
Figure 13:
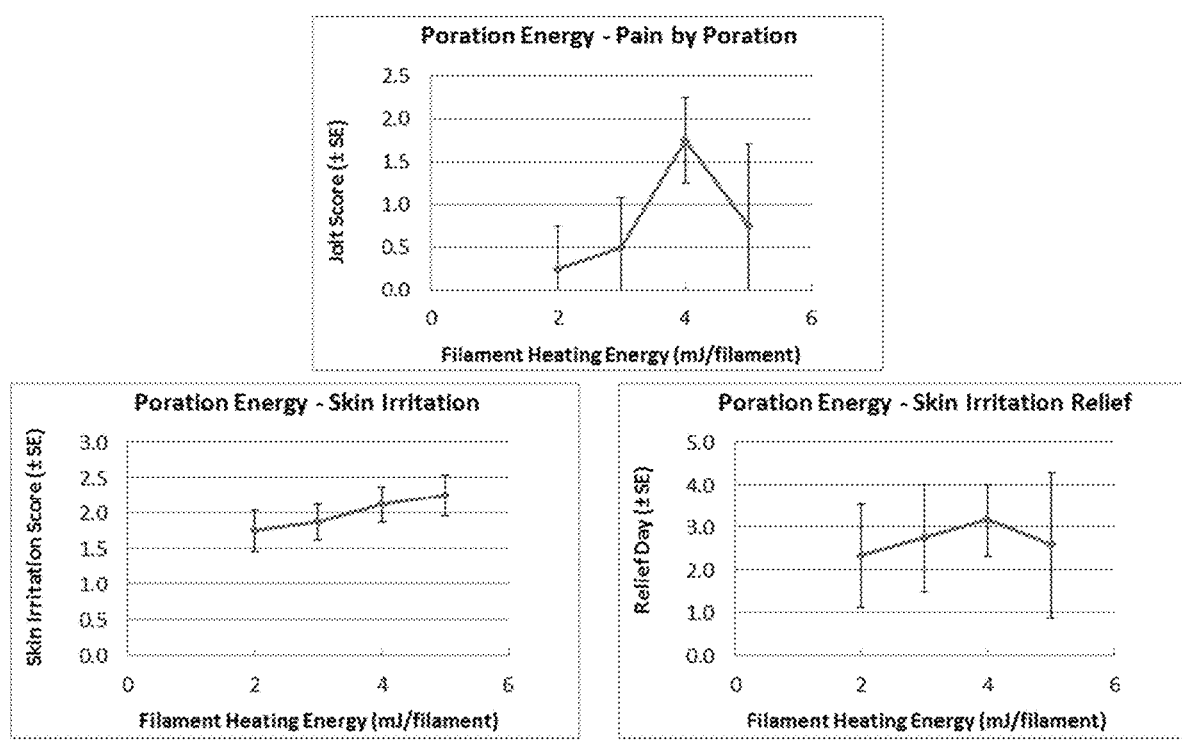
FIG. 13 illustrates relationships between poration energies and side effects.

In terms of side effects, there are no remarkable differences among the tested poration energies, as shown in the FIGS. 12 and 13. Although the higher energy might cause a little bit more sever adverse effects, it seems their scores are in the acceptable range.

In short, appropriate poration conditions have been identified depending on dose. However, filament density should be up to 400 filaments/cm$^2$ at present, and it is better to set lower filament heating energy if not necessary. For 2 mg dose formulation, 400 filaments/cm$^2$ filament density with 4 mJ/filament is the most effective among the tested conditions. The data is summarized in the Table 15.

TABLE 15

| Evaluation item | Target criteria | Result (±SE) | | | |
|---|---|---|---|---|---|
| | | # 1 | # 2 | # 3 | # 4 |
| Density (filaments/cm$^2$) | — | 400 | 400 | 400 | 400 |
| Energy (mJ/filament) | | 2 | 3 | 4 | 5 |
| n (for PK) | — | 3 | 4 | 4 | 3 |
| AUC ± SE (hr*ng/mL) | 2252 | 1492 ± 206 | 1752 ± 116 | 2103 ± 275 | 1967 ± 108 |
| Cmax ± SE (ng/mL) | 768 | 484 ± 130 | 487 ± 63 | 896 ± 191 | 752 ± 89 |
| Tmax ± SE (hours) | 2.0 | 2.33 ± 0.83 | 1.63 ± 0.13 | 1.06 ± 0.16 | 1.33± 0.33 |
| Bioavailability ± SE (%) | — | 72.4 ± 10.0 | 85.0 ± 5.6 | 102.1 ± 13.3 | 95.5 ± 5.3 |
| Pain by poration ± SD | — | 0.3 ± 0.5 | 0.5 ± 0.6 | 1.8 ± 0.5 | 0.8 ± 1.0 |
| Skin irritation ± SD (Just after patch removal) | ≤2 | 1.8 ± 0.3 | 1.9 ± 0.3 | 2.1 ± 0.3 | 2.3 ± 0.3 |
| Skin irritation relief ± SD (Days to recover to score 1) | — | 2.3 ± 1.2 | 2.8 ± 1.3 | 3.2 ± 0.8 | 2.6 ± 1.7 |

The given bioavailability of Table 15 is relative bioavailability against SC injection.

Example 9

This example describes the selection of a desirable filament array size. Assuming the higher dose than 2 mg dose with the conditions 400 filaments/cm$^2$ filament density and 4 or 5 mJ/filament energy, filament array size may need to be made bigger. The range of dose was 0.5 to 4 mg, and the range of filament array size was 1.0 to 2.0 cm$^2$. The results are summarized in Table 16.

Figure 16:
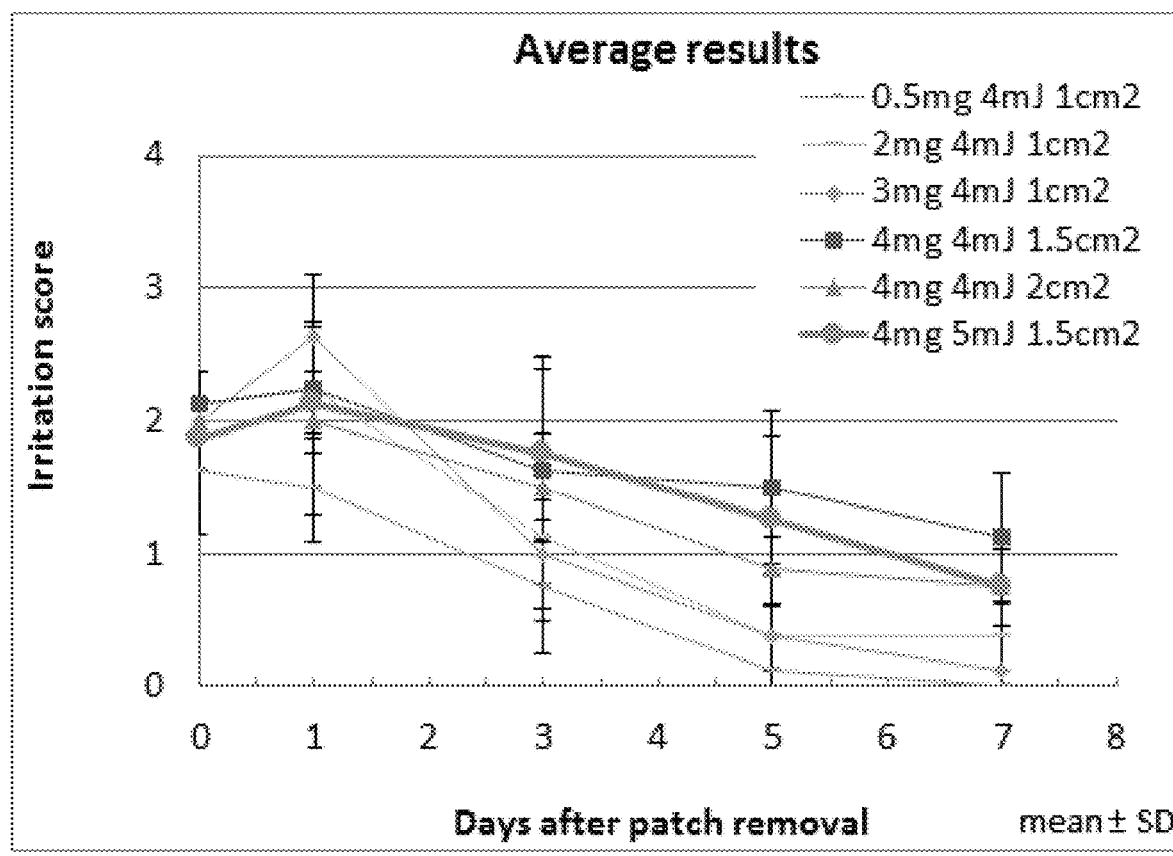
FIG. 16 illustrates skin irritation results for different filament array sizes.
Figure 17:
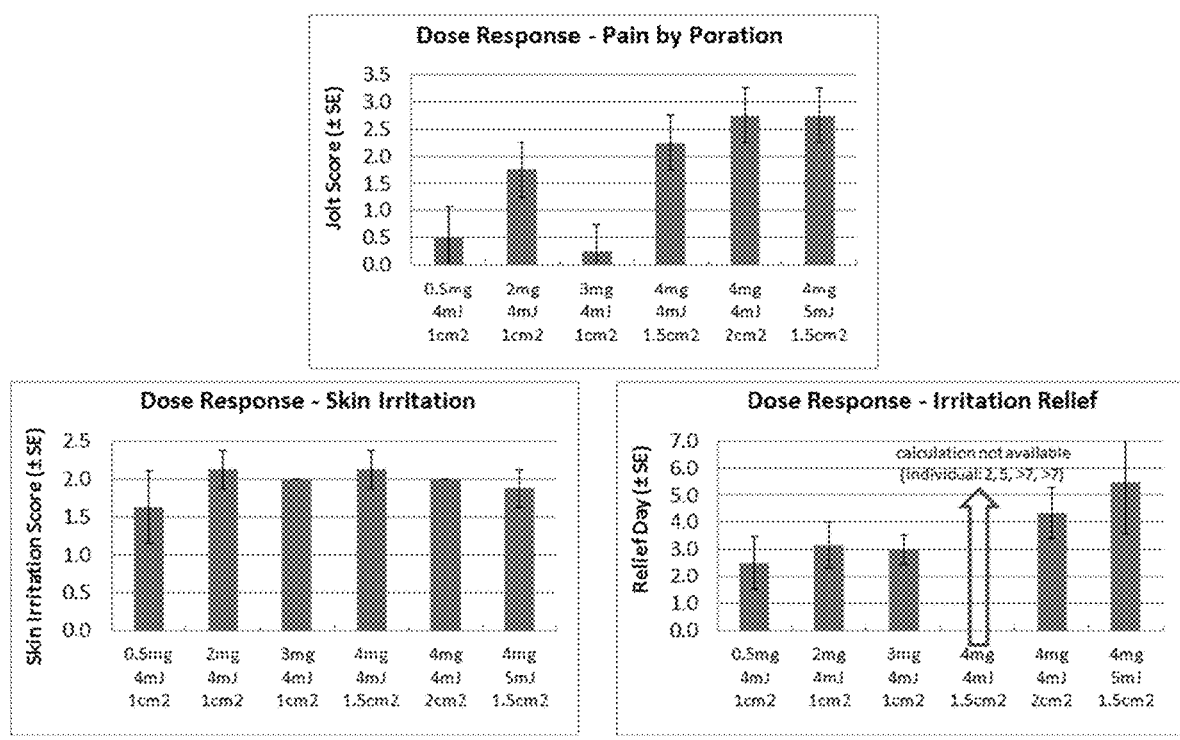
FIG. 17 illustrates relationships between dose and side effects.

With regard to side effects, it appears the wider poration area and higher energy caused a slightly more severe adverse effects as seen in the FIGS. 16 and 17. Especially, the pain by poration with 1.5 cm$^2$ and 2.0 cm$^2$ was greater.

In short summary, 2 mg dose per 1 cm$^2$ poration area is the best condition in this study when 400 filaments/cm$^2$ density and 4 mJ/filament energy are used. If the wider poration area than 1 cm$^2$ with the higher dose than 2 mg is required, the pain by poration should be taken into consideration. The data is summarized in Table 17.

TABLE 17

| Evaluation item | | # 1 | # 2 | # 3 | # 4 | # 5 | # 6 |
|---|---|---|---|---|---|---|---|
| Dose (mg) | | 0.50 | 2.00 | 3.00 | 4.00 | 4.00 | 4.00 |
| Energy (mJ/filament) | | 4 | 4 | 4 | 4 | 4 | 5 |
| Filament array area (cm$^2$) | | 1.0 | 1.0 | 1.0 | 1.5 | 2.0 | 1.5 |
| n (for PK) | | 4 | 4 | 4 | 3 | 4 | 3 |
| AUC ± SE (hr*ng/mL) | Target | 563 | 2252 | 3378 | 4504 | 4504 | 4504 |
| | Result | 364 ± 23 | 2103 ± 275 | 2347 ± 152 | 3661 ± 189 | 4312 ± 315 | 4034 ± 506 |
| Cmax ± SE (ng/mL) | Target | 768 | 768 | 768 | 768 | 768 | 768 |
| | Result | 190 ± 34 | 896 ± 191 | 756 ± 115 | 1307 ± 129 | 2205 ± 358 | 1706 ± 185 |
| Tmax ± SE (hours) | Target | 2.0 | 2.0 | 2.0 | 2.0 | 2.0 | 2.0 |
| | Result | 0.63 ± 0.13 | 1.06 ± 0.16 | 1.63 ± 0.13 | 1.33 ± 0.17 | 1.25 ± 0.14 | 0.75 ± 0.14 |
| Bioavailability ± SE (%) | | 70.6 ± 4.5 | 102.1 ± 13.3 | 76.0 ± 4.9 | 88.9 ± 4.6 | 104.6 ± 7.9 | 97.9 ± 12.3 |
| Pain by poration ± SD | | 0.5 ± 0.6 | 1.8 ± 0.5 | 0.3 ± 0.5 | 2.3 ± 0.5 | 2.8 ± 0.5 | 2.8 ± 0.5 |
| Skin irritation ± SD (Just after patch removal) | Target | ≤2 | ≤2 | ≤2 | ≤2 | ≤2 | ≤2 |
| | Result | 1.6 ± 0.5 | 2.1 ± 0.3 | 2.0 ± 0.0 | 2.1 ± 0.3 | 2.0 ± 0.0 | 1.9 ± 0.3 |
| Skin irritation relief ± SD (Days to recover to score 1) | | 2.5 1.0 | 3.2 0.8 | 3.0 0.5 | —* | 4.3 0.9 | 5.5 1.9 |

*Average could not be calculated. Individual results are 2.0, 5.0, >7.0, >7.0 (n = 4).

TABLE 16

| Conditions | | # 1 | # 2 | # 3 | # 4 | # 5 | # 6 |
|---|---|---|---|---|---|---|---|
| Poration condition | Area (cm$^2$) | 1.0 | 1.0 | 1.0 | 1.5 | 2.0 | 1.5 |
| | Density (filaments/cm$^2$) | 400 | 400 | 400 | 400 | 400 | 400 |
| | Energy (mJ/filament) | 4 | 4 | 4 | 4 | 4 | 5 |
| Formulation (mg/patch) | Zolmitriptan | 0.50 | 2.00 | 3.00 | 4.00 | 4.00 | 4.00 |
| | Sucrose | 0.50 | 0.50 | 0.50 | 0.50 | 0.50 | 0.50 |
| | Citric acid monohydrate | 0.37 | 1.46 | 2.19 | 2.93 | 2.93 | 2.93 |
| | Sodium benzoate | 0.10 | 0.10 | 0.10 | 0.15 | 0.15 | 0.15 |
| Animal study information | ID (AZOL) | 0047 | 0049 | 0047 | 0050 | 0050 | 0050 |
| | Group | 1 | 1 | 3 | 4 | 5 | 2 |

Figure 14:
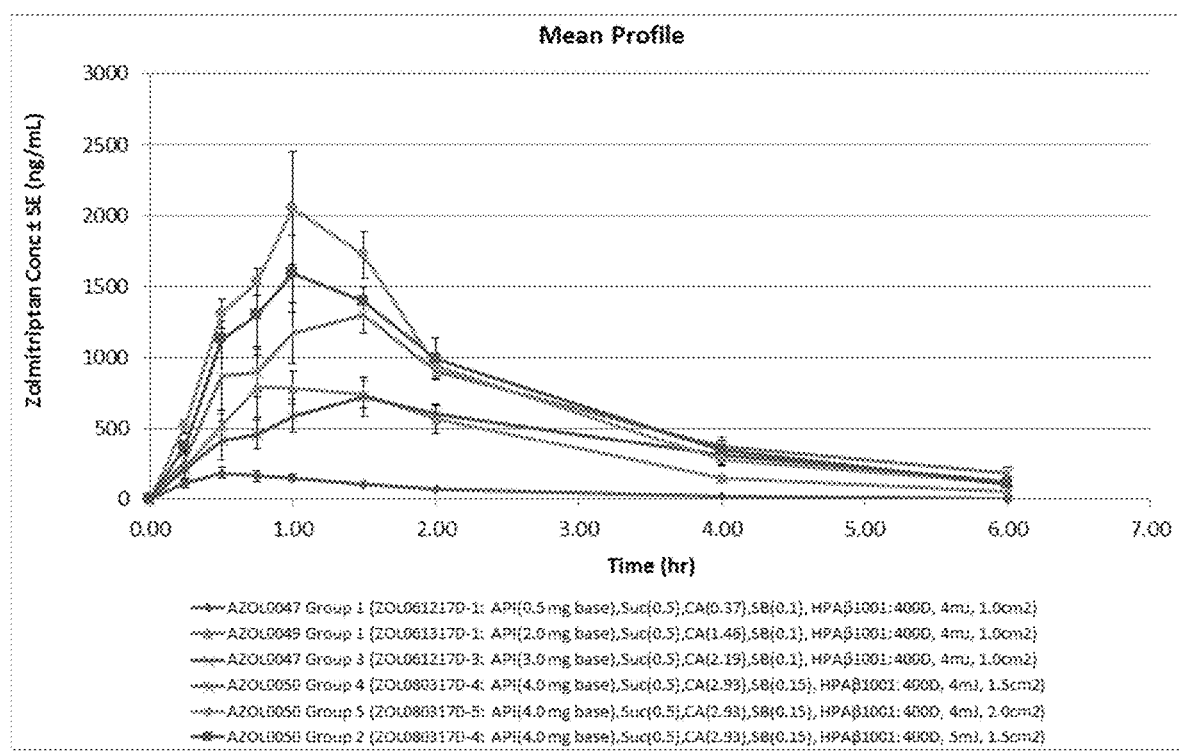
FIG. 14 illustrates PK profiles for different filament array sizes.
Figure 15:
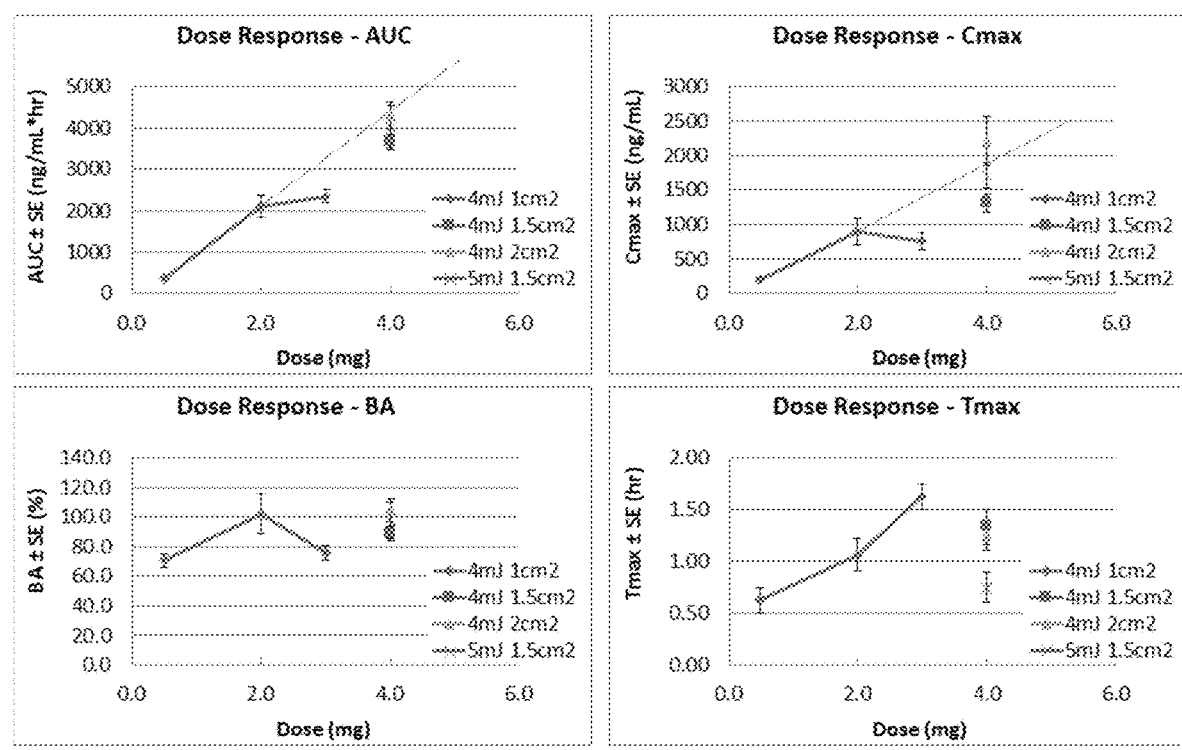
FIG. 15 illustrates dose response for different filament array size.

As described in the FIGS. 14 and 15, the PK data resulted in that 2 cm$^2$ of the filament array size demonstrated the good dose response up to 4 mg dose when utilizing 4 mJ/filament energy. 1.5 cm$^2$ was less effective for 4 mg dose. This means 2 mg dose per 1 cm$^2$ poration area is the best condition in this study for 400 filaments/cm$^2$ density with 4 mJ/filament energy. In the case of 5 mJ/filament energy, 1.5 cm$^2$ filament array size may be enough for 4 mg dose. However, the former condition (400 filaments/cm$^2$ density, 4 mJ/filament, 2 cm$^2$) is better than the latter condition (400 filaments/cm$^2$ density, 5 mJ/filament, 1.5 cm$^2$) for 4 mg dose.

The given bioavailability of Table 17 is relative bioavailability against SC injection.

Example 10

Figure 18:
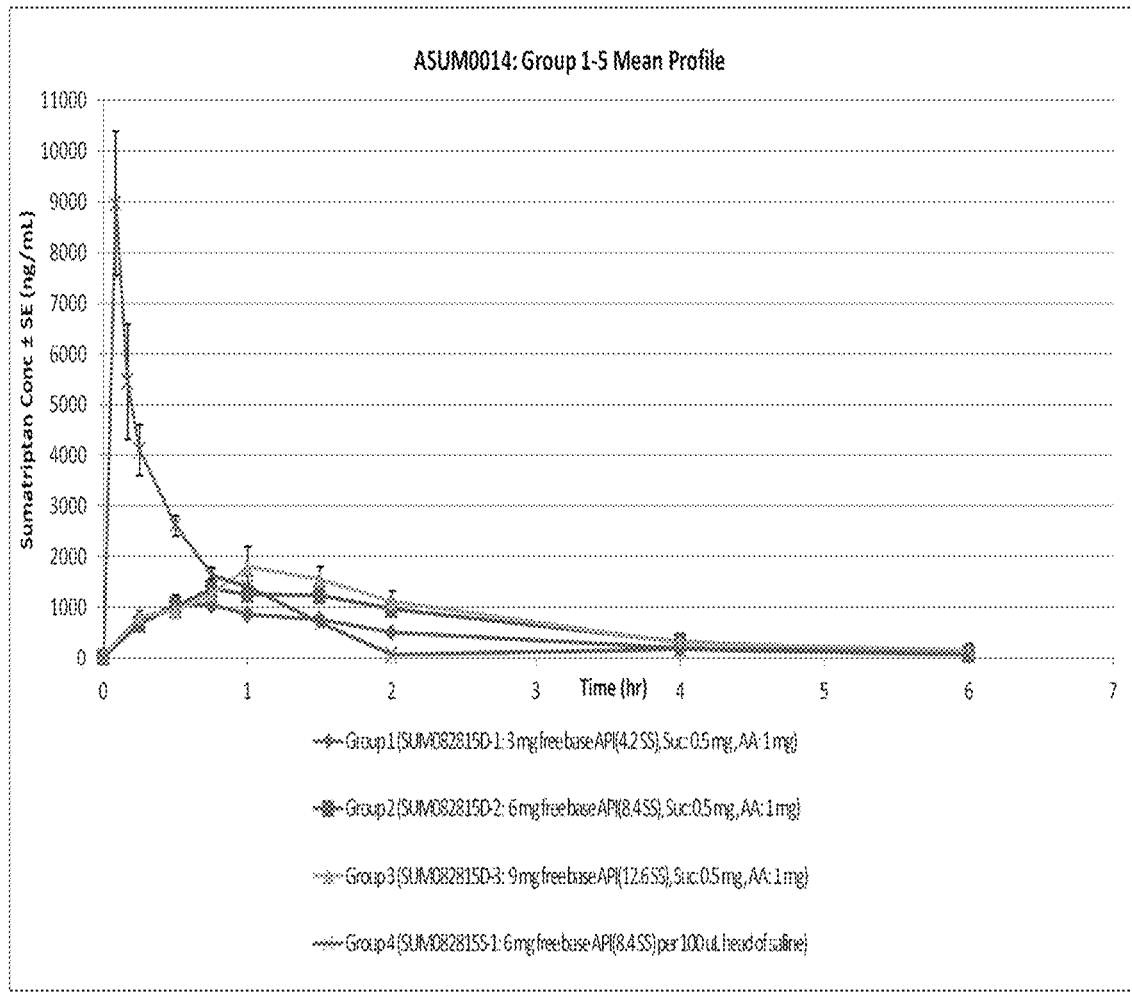
FIG. 18 illustrates results comparing a subcutaneous injection route with a transdermal microporation system.

This example describes an administration route study in hairless rats with Sumatriptan Succinate. In this study, four groups of hairless rats were tested under the following conditions: (1) Group 1 (3 mg free base API, Suc: 0.5 mg, AA: 1 mg); (2) Group 2 (6 mg free base API, Suc: 0.5 mg, AA: 1 mg); (3) Group 3 (9 mg free base API, Suc: 0.5 mg, AA: 1 mg); and (4) Group 4 (6 mg free base API per 100 μL head of saline). In the context of these investigations, the term "free base" refers to the weight of Sumatriptan free base present (e.g., with reference to Example 1, 4.2 mg Sumatriptan Succinate was used, which contained 3.0 mg sumatriptan free base). Additionally, for example with reference to FIG. 18, "4.2 SS" refers to the presence of 4.2 mg Sumatriptan Succinate. Poration condition of transdermal microporation and the matrix of the drug patch was same as the Group 4 of Example 4. The results are summarized in FIG. 18 and Table 18.

TABLE 18

| Group | AUC (ng/ml*hr) | BA (%) | Cmax (ng/mL) | Tmax (hr) |
|---|---|---|---|---|
| 1 | 2598.5 | 96.5 | 1035.3 | 0.8 |
| 2 | 3814.5 | 70.9 | 1404.9 | 1.3 |
| 3 | 4388.9 | 54.4 | 1582.6 | 1.1 |
| 4 | 5383.5 | 100.0 | 9780.9 | 0.08 |

The given bioavailability of Table 18 is relative bioavailability against SC injection.

What is claimed is:

1. A patch for delivering a triptan drug to a subject in need thereof, comprising:
   a top layer comprising an adhesive;
   a middle layer comprising a triptan, a skin irritation reducer, an anti-microbial agent, and a stabilizer; and
   a bottom layer, wherein the bottom layer comprises a release liner.

2. The patch of claim 1, wherein the stabilizer is in an amount in a range from about 0.01 g/cm$^2$ to about 0.5 g/cm$^2$.

3. The patch of claim 1, wherein the molar ratio of the amounts of the triptan and skin irritation reducer are in a ratio from about 1:0.5 to about 1:2.

4. The patch of claim 1, wherein the triptan is selected from sumatriptan, rizatriptan, or zolmitriptan.

5. The patch of claim 1, wherein the skin irritation reducer is an organic acid or salt thereof.

6. The patch of claim 5, wherein the organic acid is selected from ascorbic acid, citric acid, succinic acid, tartaric acid, maleic acid, lactic acid, benzoic acid, and sorbic acid or a combination thereof.

7. The patch of claim 2, wherein the stabilizer is a saccharide.

8. The patch of claim 7, wherein the saccharide is selected from mannitol, maltose, trehalose, xylitol, xylose, dextrose, lactose, sorbitol, sucrose, fructose, maltitol, erythritol, lactitol, isomalt, and cyclodextrins or a combination thereof.

9. The patch of claim 1, wherein the middle layer further comprises a reservoir that is configured to contain the triptan.

10. The patch of claim 9, wherein the reservoir comprises a matrix.

11. The patch of claim 10, wherein the matrix has a water holding capacity in the range from about 0.1 mg/cm$^2$ to about 10 mg/cm$^2$.

12. The patch of claim 1, wherein the anti-microbial agent is selected from at least one of benzoic acid, sodium benzoate, methyl paraben, propyl paraben, benzalkonium chloride, chlorhexidine, cresol, salicylic acid, sorbic acid, and benzetonium chloride, or combination thereof.

13. The patch of claim 1, wherein the skin irritation reducer is a non-organic acid or salt thereof.

14. The patch of claim 13, wherein the non-organic acid is selected from hydrochloric acid, phosphoric acid, boric acid, and acetic acid.

15. The patch of claim 10, wherein the triptan is zolmitrptan and the matrix comprises about 0.1 to about 5.0 mg/cm$^2$ zolmitriptan.

16. The patch of claim 4, wherein the amounts of the zolmitriptan and the skin irritation reducer are in a ratio from about 1:0.75 to about 1:1.5.

17. The patch of claim 10, wherein the matrix comprises zolmitriptan and the stabilizer in a total amount per unit area of the matrix that is in a range of 0.05 to 0.5 mg/cm$^2$.

18. A method of treating a subject in need thereof, comprising:
   identifying a subject having a migraine;
   opening a plurality of micropores in the skin of the subject;
   applying a patch to the subject's skin over the micropore for a period of time, wherein the patch comprises:
   a top layer comprising an adhesive;
   a middle layer comprising a triptan, a skin irritation reducer, an anti-microbial agent, and a stabilizer; and
   a bottom layer, wherein the bottom layer comprises a release liner, wherein the period of time is selected to deliver a therapeutically effective amount of the triptan through the plurality of micropores.

19. A transdermal drug delivery patch system for delivering a drug, comprising:
   a transdermal microporation apparatus for heating a skin surface; and
   a triptan drug delivery patch,
   wherein the drug delivery patch comprises
   a top layer comprising an adhesive,
   a middle layer comprising a triptan, a skin irritation reducer, an anti-microbial agent, and a stabilizer; and
   a bottom layer, wherein the bottom layer comprises a release liner.

20. The patch of claim 19, wherein the anti-microbial agent is selected from at least one of benzoic acid, sodium benzoate, methyl paraben, propyl paraben, benzalkonium chloride, chlorhexidine, cresol, salicylic acid, sorbic acid, and benzetonium chloride, or combination thereof.

* * * * *

UNITED STATES PATENT AND TRADEMARK OFFICE
CERTIFICATE OF CORRECTION

PATENT NO. : 11,638,809 B2
APPLICATION NO. : 16/911181
DATED : May 2, 2023
INVENTOR(S) : Hirotoshi Adachi et al.

It is certified that error appears in the above-identified patent and that said Letters Patent is hereby corrected as shown below:

On the Title Page

Column 2, Line 1, Item (56) under Other Publications, delete "Met a/" and insert --M et al--.

Column 2, Line 4, Item (56) under Other Publications, delete "etal" and insert --et al--.

In the Specification

In Column 2, Lines 25-26, delete "desquamination" and insert --desquamation--.

In Column 3, Line 59, delete "benzetonium" and insert --benzethonium--.

In Column 9, Line 64, delete "tripans" and insert --triptans--.

In Column 10, Line 19, delete "anticoagulents" and insert --anticoagulants--.

In Column 13, Line 21, delete "benzetonium" and insert --benzethonium--.

In Columns 15-16, Table 3, Line 56 (approx.), delete "Sue," and insert --Suc,--.

In Column 18, Line 35 (approx.), delete "mg/cm$^2$)," and insert --mg/cm$^2$).--.

In Column 18, Line 54 (approx.), delete "Zomitriptan." and insert --Zolmitriptan.--.

In the Claims

In Column 28, Claim 12, Line 3, delete "benzetonium" and insert --benzethonium--.

Signed and Sealed this
Tenth Day of October, 2023

Katherine Kelly Vidal
*Director of the United States Patent and Trademark Office*

In Column 28, Claim 15, Lines 9-10, delete "zolmitrptan" and insert --zolmitriptan--.

In Column 28, Claim 20, Line 47 (approx.), delete "benzetonium" and insert --benzethonium--.